United States Patent
Oba et al.

(10) Patent No.: US 9,541,533 B2
(45) Date of Patent: Jan. 10, 2017

(54) GAS SENSOR

(71) Applicant: NGK SPARK PLUG CO., LTD., Nagoya-shi, Aichi (JP)

(72) Inventors: Takehiro Oba, Konan (JP); Shingo Ito, Ichinomiya (JP); Makoto Kume, Inuyama (JP); Daisuke Tahira, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 233 days.

(21) Appl. No.: 14/168,630

(22) Filed: Jan. 30, 2014

(65) Prior Publication Data
US 2014/0224044 A1    Aug. 14, 2014

(30) Foreign Application Priority Data

Feb. 8, 2013    (JP) ................................ 2013-023680
Feb. 8, 2013    (JP) ................................ 2013-023683
Oct. 30, 2013    (JP) ................................ 2013-225507

(51) Int. Cl.
   G01N 27/407    (2006.01)
   G01N 33/00    (2006.01)

(52) U.S. Cl.
   CPC ........ *G01N 33/0009* (2013.01); *G01N 27/407* (2013.01)

(58) Field of Classification Search
   CPC ........................... G01N 33/0009; G01N 27/407
   See application file for complete search history.

(56) References Cited

U.S. PATENT DOCUMENTS 4,505,807 A * 3/1985 Yamada ............... G01N 27/417
                                                            204/412
4,588,494 A * 5/1986 Kato .................. G01N 27/4062
                                                            204/426
(Continued)

FOREIGN PATENT DOCUMENTS

JP        10-253579 A      9/1998
JP      2002-207023 A      7/2002
(Continued)

OTHER PUBLICATIONS

Communication dated Jul. 21, 2015 from the Japanese Patent Office issued in corresponding Japanese application No. 2013-225507.
(Continued)

*Primary Examiner* — Lisa Caputo
*Assistant Examiner* — Punam Roy
(74) *Attorney, Agent, or Firm* — Sughrue Mion, PLLC

(57) ABSTRACT

A gas sensor (1) has a platelike detection element (5) extending in an axial direction and a ceramic member (67) having an element insertion hole (81) into which the detection element (5) is inserted. When the ceramic member (67) is viewed from the axial direction, the element insertion hole (81) has a main insertion hole (83) having a substantially quadrate shape surrounded by four sides, and relief holes (85), (86), (87) and (88), each of which is surrounded by an outline connecting ends of two adjacent sides of the four sides of the main insertion hole (83) and located radially outward of the main insertion hole (83) so as to communicate with the main insertion hole 83.

10 Claims, 18 Drawing Sheets

(56) References Cited

U.S. PATENT DOCUMENTS

| | | | | |
|---|---|---|---|---|
| 4,818,363 | A | * | 4/1989 | Bayha ................ G01N 27/4062 204/426 |
| 5,246,562 | A | * | 9/1993 | Weyl ................ G01N 27/4078 204/424 |
| 5,429,737 | A | * | 7/1995 | Pribat ................ G01N 27/4071 204/424 |
| 5,573,650 | A | * | 11/1996 | Fukaya ................ G01N 27/407 204/400 |
| 6,082,175 | A | | 7/2000 | Yoshikawa et al. |
| 6,613,206 | B1 | * | 9/2003 | Weyl ................ G01N 27/407 204/421 |
| 6,688,157 | B2 | * | 2/2004 | Yamada ................ G01N 27/4075 204/424 |
| 6,851,180 | B2 | * | 2/2005 | Hattori ................ G01N 27/4062 204/424 |
| 6,866,517 | B2 | * | 3/2005 | Kimata ................ H01R 12/721 439/33 |
| 7,032,433 | B2 | * | 4/2006 | Hayashi ................ G01N 27/407 204/424 |
| 7,191,640 | B2 | * | 3/2007 | Weyl ................ G01K 1/14 374/E1.018 |
| 7,340,942 | B2 | * | 3/2008 | Matsuo ................ G01N 27/4062 73/31.05 |
| 7,637,145 | B2 | * | 12/2009 | Yamauchi ................ G01N 27/407 73/31.05 |
| 2006/0237315 | A1 | | 10/2006 | Matsuo et al. |
| 2007/0089486 | A1 | | 4/2007 | Yamauchi et al. |
| 2014/0224044 | A1 | | 8/2014 | Oba et al. |
| 2015/0114085 | A1 | | 4/2015 | Iwano et al. |

FOREIGN PATENT DOCUMENTS

| | | | | | |
|---|---|---|---|---|---|
| JP | 2005-106691 | A | | 4/2005 | |
| JP | 2005-134345 | A | | 5/2005 | |
| JP | 2006-308328 | A | | 11/2006 | |
| JP | 2006-337096 | A | | 12/2006 | |
| JP | 2007-003216 | A | | 1/2007 | |
| JP | 2007-24670 | A | | 2/2007 | |
| JP | 2007-047075 | A | | 2/2007 | |
| JP | 2007-127619 | A | | 5/2007 | |
| JP | 2012230076 | A | * | 11/2012 | |
| JP | 2013181769 | A | * | 9/2013 | |
| JP | WO 2013128801 | A1 | * | 9/2013 | ......... G01N 27/4077 |
| JP | 2013210358 | A | * | 10/2013 | |
| JP | 2014-153219 | A | | 8/2014 | |
| JP | 2014-169991 | A | | 9/2014 | |
| JP | 2015-087161 | A | | 5/2015 | |

OTHER PUBLICATIONS

Communication dated Apr. 14, 2015 from the Japanese Patent Office in counterpart application No. 2013-023680.

* cited by examiner

GAS SENSOR

BACKGROUND OF THE INVENTION

1. Field of the Invention

The present invention relates to a gas sensor having ceramic members, such as a holder, a sleeve and a separator, and used as, for example, an air/fuel ratio sensor.

2. Description of the Related Art

Conventionally, an air/fuel ratio sensor, for example, includes the following ceramic members: a holder through which a platelike gas detection element (hereinafter, referred to as a detection element) is inserted and which is engaged with a forward portion of the gas detection element; a sleeve through which the detection element is inserted and which is engaged with a central portion of the detection element; and a separator which accommodates a rear end portion of the detection element and into which connection terminals made of metal are inserted (refer to Patent Documents 1 and 2).

Among the above-mentioned ceramic members, as shown in FIG. 20, the holder and the sleeve have, for example, an element insertion hole P2 through which a detection element P1 (having a substantially rectangular cross section) is inserted. FIG. 20 is a view of the sleeve as viewed from the direction of the axial line of the detection element P1. The element insertion hole P2 has a substantially quadrate shape surrounded by four sides; however, corners P3 of the element insertion hole P2 are not right-angled (at an angle of 90 degrees), but are radiused; i.e., smoothly curved. This is for the following reason: as a result of employing right-angled corners P3, stress is apt to be imposed on the apexes of the corners P3, potentially generating cracks in the ceramic member.

[Patent Document 1] Japanese Patent Application Laid-Open (kokai) No. 2006-308328

[Patent Document 2] Japanese Patent Application Laid-Open (kokai) No. 2007-3216

3. Problems to be Solved by the Invention

However, when the edges P3 of the element insertion hole P2 are radiused, as shown in FIG. 20, the dimensions (vertical dimension T1 and horizontal dimension T2) of the element insertion hole P2 must be greater than the dimensions (specifically, thickness t1 and width t2) of the detection element P1 to be inserted into the element insertion hole P2.

This is for the following reason: when the platelike detection element P1 is to be inserted into the element insertion hole P2, the radiused surfaces of corners P3 of the element insertion hole P2 must be located radially outward of the apexes of edges P4 of the platelike detection element P1.

As a result, a clearance between the side surfaces of the detection element P1 and the inner peripheral surfaces of the element insertion hole P2 increases, thereby raising a problem in that the detection element P1 is apt to have play within the element insertion hole P2, with a resultant deterioration in positioning accuracy.

Although unillustrated, in the case of the separator, when the connection terminals are to be disposed through insertion into terminal insertion holes, similar to the above-mentioned case, since the edges of the terminal insertion holes are radiused, a problem arises in that the connection terminals are apt to have play, with a resultant deterioration in positioning accuracy.

SUMMARY OF THE INVENTION

The present invention has been made to solve the above problems, and an object thereof is to provide a gas sensor in which generation of cracks in the edges of the ceramic members is prevented, while play of the detection element and the connection terminals is reduced by implementing appropriate clearances for inserting the detection element and the connection terminals into the element insertion hole and the terminal insertion holes of the ceramic members.

The above object, according to a first aspect (1) of the present invention, is achieved by providing a gas sensor which comprises a platelike detection element extending in an axial direction and a ceramic member having an element insertion hole into which the detection element is inserted. In the gas sensor, when the ceramic member is viewed from the axial direction, the element insertion hole has a main insertion hole having a substantially quadrate shape surrounded by four sides, and a relief hole surrounded by an outline connecting ends of two adjacent sides of the four sides of the main insertion hole, and located radially outward of the main insertion hole so as to communicate with the main insertion hole.

In the gas sensor of the first aspect (1), the element insertion hole of the ceramic member has a relief hole which is surrounded by an outline connecting the ends of two adjacent sides of the four sides of the main insertion hole and is located radially outward of the main insertion hole so as to communicate with the main insertion hole. By virtue of the presence of the relief hole, the main insertion hole does not have a radiused edge. Therefore, dimensions (width and thickness) of the detection element to be inserted into the main insertion hole can be substantially equal to the dimensions (vertical dimension and horizontal dimension) of the main insertion hole. As a result, the clearance between a side surface of the detection element and a corresponding inner peripheral surface of the element insertion hole can be made small, thereby reducing play of the detection element within the element insertion hole.

Examples of the substantially quadrate shape include a quadrate shape (rectangular shape). In the case where the substantially quadrate shape has an edge(s) where no relief hole is formed, the edge may be chamfered or radiused. That is, the substantially quadrate shape may encompass one having a chamfered or radiused edge(s) (the same also applies in the following description).

In a preferred embodiment (2) of the gas sensor (1) above, of the two sides of the main insertion hole connected to the outline of the relief hole, one side reaches an intersection with an extension line of the other side.

In the gas sensor (2), of the two sides of the main insertion hole connected to the outline of the relief hole, one side reaches an intersection with an extension line of the other side. Thus, an inner peripheral surface of the main insertion hole which includes the one side can face a corresponding side surface of the detection element over substantially the entire longitudinal direction of the one side, thereby further reducing play of the detection element within the element insertion hole. Incidentally, since the extension line of the other side intersects with the one side, the end of the other side does not reach the intersection.

In a preferred embodiment (3) of the gas sensor (2) above, the outline of the relief hole is smoothly formed from the end of the one side to the end of the other side.

The gas sensor (3) has the following advantage: since the relief hole is smoothly formed, cracks are unlikely to generate in the ceramic member, so that the ceramic member can maintain its strength.

In another preferred embodiment (4) of the gas sensor (1) above, the two sides of the main insertion hole connected to the outline of the relief hole do not reach an intersection of extension lines of the two sides, and an area of the relief hole is greater than an area of a triangle surrounded by the extension lines of the two sides of the main insertion hole and a straight line connecting the ends of the two sides of the main insertion hole.

In the gas sensor (4), the two sides of the main insertion hole which are connected to the outline of the relief hole do not reach an intersection of extension lines of the two sides, and the area of the relief hole is greater than the area of a triangle surrounded by the extension lines of the two sides and a straight line that connects the ends of the two sides of the main insertion hole. Thus, the relief hole protrudes further radially outward of the main insertion hole. As a result, the shortest distance between the outline of the relief hole and the intersection of the extension lines increases. Therefore, when the detection element is inserted into the main insertion hole, contact of an edge of the detection element with the outline of the relief hole can be reliably prevented.

Also, since the ends of the two sides of the main insertion hole which are connected to the outline of the relief hole further approach each other, the two sides can be increased in length. Therefore, the two inner peripheral surfaces of the main insertion hole, which include the two sides, face two corresponding side surfaces of the detection element over respectively increased ranges, thereby further reducing play of the detection element within the element insertion hole.

The area of the relief hole is a differential area yielded by subtracting the area of the main insertion hole from the area of the element insertion hole; specifically, an area surrounded by the extension lines of the two sides of the main insertion hole and the outline of the relief hole.

In a preferred embodiment (5) of the gas sensor (4) above, the outline of the relief hole is smoothly formed.

The gas sensor (5) has the following advantage: since the relief hole is smoothly formed, cracks are unlikely to generate in the ceramic member, so that the ceramic member can maintain its strength.

In a second aspect (6), the above object of the present invention is achieved by providing a gas sensor which comprises a platelike detection element extending in an axial direction and a ceramic member surrounding a rear end portion of the detection element and having a substantially quadrate element insertion hole into which the detection element is inserted, and a terminal insertion hole which is located radially outward of the element insertion hole and communicates with the element insertion hole and into which a connection terminal electrically connected to the detection element is inserted. In the gas sensor (6), when the ceramic member is viewed from the axial direction, the terminal insertion hole has a main insertion hole having a substantially polygonal shape surrounded by a plurality of sides, and a relief hole surrounded by an outline connecting ends of two adjacent sides of the plurality of sides of the main insertion hole, and located radially outward of the main insertion hole so as to communicate with the main insertion hole.

In the gas sensor (6), the terminal insertion hole of the ceramic member has a relief hole which is surrounded by the outline connecting the ends of two adjacent sides of the plurality of sides of the main insertion hole and is located radially outward of the main insertion hole so as to communicate with the main insertion hole. By virtue of the presence of the relief hole, the main insertion hole does not have a radiused edge. Therefore, the dimensions (width and thickness) of the connection terminal to be inserted into the main insertion hole can be substantially equal to the dimensions (vertical dimension and horizontal dimension) of the main insertion hole. As a result, a clearance between a side surface of the connection terminal and a corresponding inner peripheral surface of the terminal insertion hole can be small, thereby reducing play of the connection terminal within the terminal insertion hole.

Examples of the substantially polygonal shape include a polygonal shape. In the case where the substantially polygonal shape has an edge(s) where no relief hole is formed, the edge may be chamfered or radiused. That is, the substantially polygonal shape may encompass one having a chamfered or radiused edge(s).

In a preferred embodiment (7) of the gas sensor (6) above, of the two sides of the main insertion hole connected to the outline of the relief hole, one side reaches an intersection with an extension line of the other side.

In the gas sensor (7), of the two sides of the main insertion hole connected to the outline of the relief hole, one side reaches an intersection with an extension line of the other side. Thus, the inner peripheral surface of the main insertion hole which includes the one side can face a corresponding side surface of the connection terminal over substantially the entire longitudinal direction of the one side, thereby reducing play of the connection terminal within the terminal insertion hole.

In a preferred embodiment (8) of the gas sensor (7) above, the outline of the relief hole is smoothly formed from the end of the one side to the end of the other side.

The gas sensor (8) has the following advantage: since the relief hole is smoothly formed, cracks are unlikely to generate in the ceramic member, so that the ceramic member can maintain its strength.

In a preferred embodiment (9) of the gas sensor (6) above, the two sides of the main insertion hole connected to the outline of the relief hole do not reach an intersection of extension lines of the two sides, and an area of the relief hole is greater than an area of a triangle surrounded by the extension lines of the two sides of the main insertion hole and a straight line connecting the ends of the two sides of the main insertion hole.

In the gas sensor (9), the two sides of the main insertion hole which are connected to the outline of the relief hole do not reach an intersection of extension lines of the two sides, and the area of the relief hole is greater than the area of a triangle surrounded by the extension lines of the two sides and a straight line that connects the ends of the two sides of the main insertion hole. Thus, the relief hole protrudes further radially outward of the main insertion hole. As a result, the shortest distance between the outline of the relief hole and the intersection of the extension lines increases. Therefore, when the connection terminal is inserted into the main insertion hole, contact of an edge of the connection terminal with the outline of the relief hole can be reliably prevented.

Also, since the ends of the two sides of the main insertion hole which are connected to the outline of the relief hole further approach each other, the two sides can be increased in length. Therefore, the two inner peripheral surfaces of the main insertion hole, which include the two sides, face two corresponding side surfaces of the connection terminal over respectively increased ranges, thereby further reducing play of the connection terminal within the terminal insertion hole.

The area of the relief hole is a differential area obtained by subtracting the area of the main insertion hole from the area of the terminal insertion hole. Specifically, this is an area surrounded by the extension lines of the two sides of the main insertion hole and the outline of the relief hole.

In a preferred embodiment (10) of the gas sensor (9) above, the outline of the relief hole is smoothly formed.

The gas sensor (10) has the following advantage: since the relief hole is smoothly formed, cracks are unlikely to generate in the ceramic member, so that the ceramic member can maintain its strength.

DESCRIPTION OF REFERENCE NUMERALS

Figure 1:
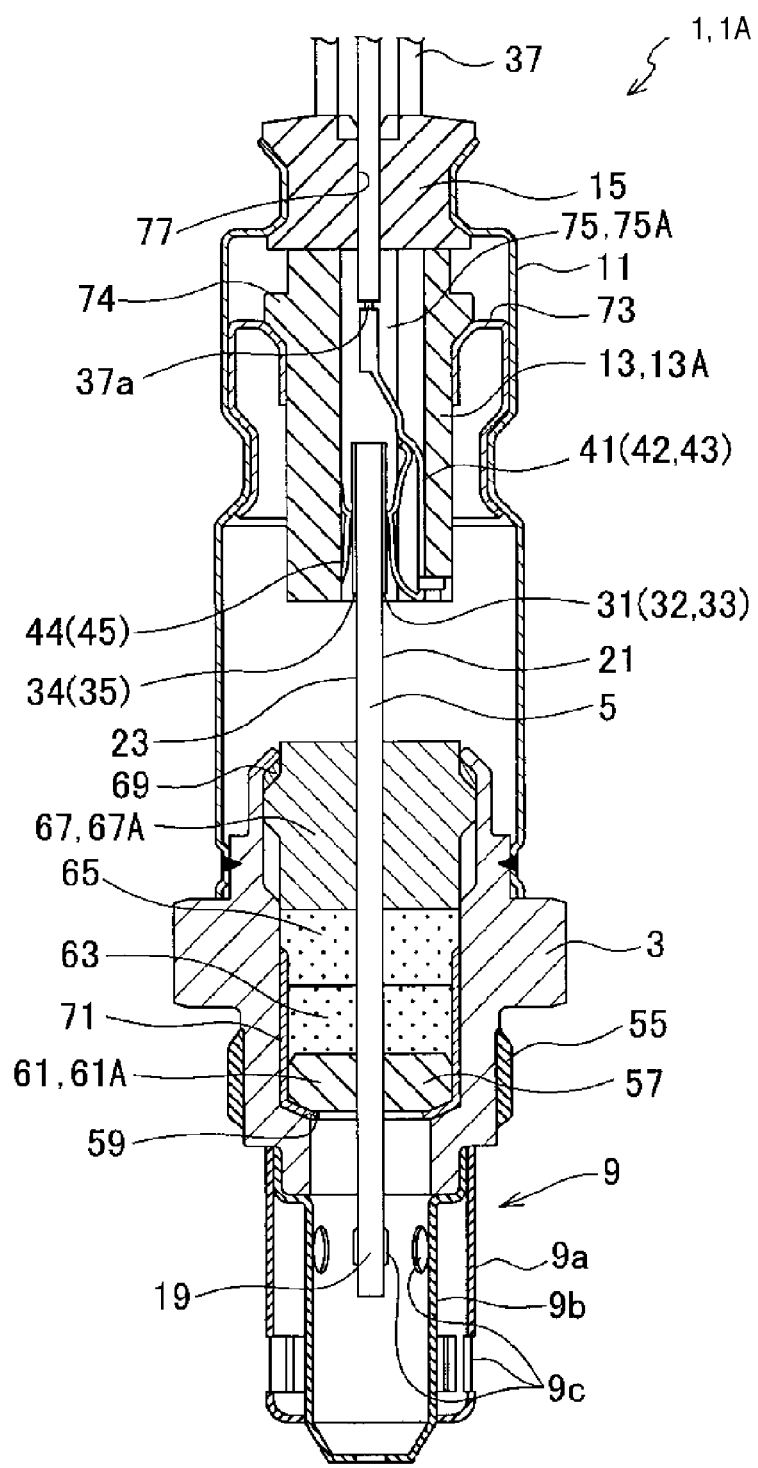
FIG. 1 is a sectional view showing the overall configuration of an air/fuel ratio sensor according to first and second embodiments of the present invention.

Reference numerals used to identify various features in the drawings include the following.
1, 1A: air/fuel ratio sensor
5: detection element
13, 13A: ceramic separator (ceramic member)
41, 42, 43, 44, 45: connection terminal
61, 61A: ceramic holder (ceramic member)
67, 67A: ceramic sleeve (ceramic member)
81, 101, 110, 81*a*, 101A, 110A: element insertion hole
111, 112, 113, 114, 115, 111A, 112A, 113A, 114A, 115A: terminal insertion hole

DETAILED DESCRIPTION OF THE PREFERRED EMBODIMENTS

Next, ceramic members for carrying out the present invention (first and second embodiments) will be described in detail with reference to the drawings. However, the present invention should not be construed as being limited thereto.

More particularly, the first and second embodiments will be described with reference to a full range air/fuel ratio sensor (hereinafter, also called an air/fuel ratio sensor). The sensor is attached to, for example, an exhaust pipe of an internal combustion engine for performing air/fuel ratio feedback control of automobiles and various internal combustion engines and to which a detection element (gas sensor element) is attached for detecting a particular gas contained in an exhaust gas to be measured.

First Embodiment a) First, the overall configuration of an air/fuel ratio sensor will be described.

As shown in FIG. 1, an air/fuel ratio sensor 1 includes a tubular metallic shell 3 fixed mainly to an exhaust pipe (not shown); a platelike detection element 5 inserted through the metallic shell 3 and extending in an axial direction (the longitudinal direction of the air/fuel ratio sensor 1 or the vertical direction in FIG. 1); a protector 9 disposed at a forward end portion (lower end portion in FIG. 1) of the metallic shell 3 and covering a forward end portion of the detection element 5; a tubular casing 11 attached to a rear end portion (upper end portion in FIG. 1) of the metallic shell 3 and covering the outer circumference of the detection element 5; a separator (ceramic separator) 13 disposed within the tubular casing 11 and accommodating therein a rear end portion of the detection element 5; and a closing member 15 for closing the rear end of the tubular casing 11.

Configurational features are described below.

The detection element 5 is configured as follows: a detection portion 19 covered with a protection layer is formed at its forward end portion oriented toward a gas to be measured, and electrode terminals (first to fifth electrode terminals) 31, 32, 33, 34 and 35 are formed on a first plate surface 21 and a second plate surface 23. The first and second plate surfaces 21 and 23 define outer surfaces of a rear end portion of the detection element 5 and are in a front-back relation with each other.

The detection element 5 is fixed within the metallic shell 3 such that the detection portion 19 at its forward end portion protrudes from the forward end of the metallic shell 3 fixed to the exhaust pipe and the electrode terminals 31 to 35 at the rear end portion of the detection element 5 protrude from the rear end of the metallic shell 3.

Metal terminals; specifically, connection terminals (first to fifth terminals) 41, 42, 43, 44 and 45 are connected to the electrode terminals 31 to 35, respectively. That is, the connection terminals 41 to 45 are disposed within the ceramic separator 13 between the detection element 5 and the ceramic separator 13 and are thereby electrically connected to the electrode terminals 31 to 35, respectively, of the detection element 5. Further, the connection terminals 41 to 45 are formed of an elastic heat resistant metal, such as stainless steel.

The connection terminals 41 to 45 are electrically connected to (five) lead wires 37 (specifically, core wires 37a in the lead wires 37), respectively, extending from an external apparatus into the sensor and form current paths for electric current flowing between the electrode terminals 31 to 35 and the external apparatus, to which the lead wires 37 are connected (in FIG. 1, only three lead wires 37 are shown).

Figure 2:
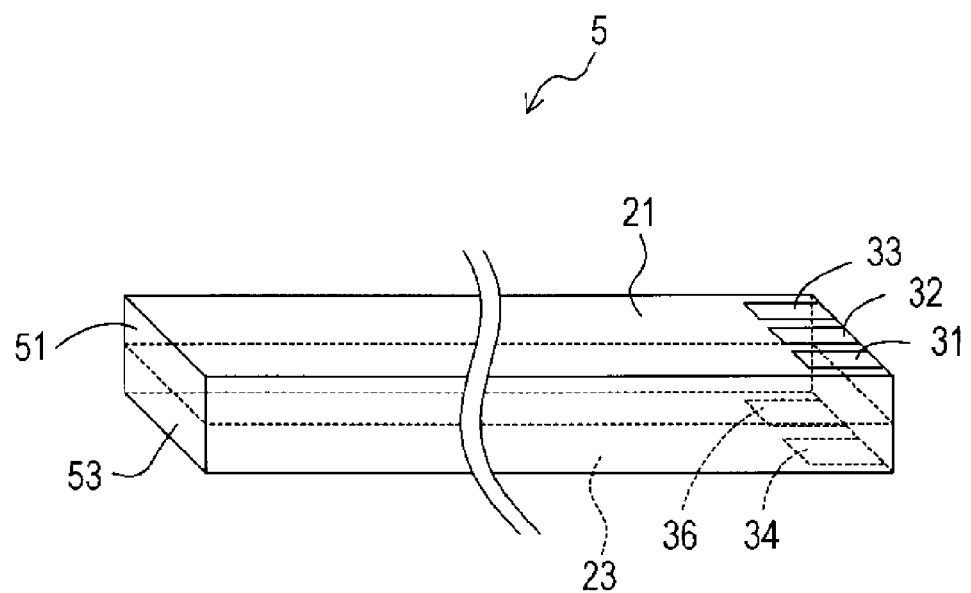
FIG. 2 is a perspective view showing a schematic structure of a detection element used in the air/fuel ratio sensor according to the first and second embodiments.

As shown in FIG. 2, the detection element 5 has a rectangular parallelepiped shape configured such that a platelike element section 51 extending in the axial direction (in FIG. 2, the horizontal direction) and a platelike heater 53 extending in the axial direction are laminated together, and has a quadrate cross section (in the present embodiment, 1.2 mm thickness×4.2 mm width) taken perpendicularly to the axial direction.

Since the detection element 5 used in the air/fuel sensor 1 is a conventionally known one, a detailed description of its internal structure, etc., is omitted, and its schematic configuration is as follows.

First, the element section 51 is composed of an oxygen concentration cell element configured such that porous electrodes are formed respectively on opposite sides of a solid electrolyte substrate; an oxygen pump element configured such that porous electrodes are formed respectively on opposite sides of a solid electrolyte substrate; and a spacer sandwiched between these two elements for forming a hollow measuring gas chamber. The solid electrolyte substrate is formed of zirconia which contains yttria as a stabilizer in solid solution, and the porous electrodes are formed primarily of Pt. The spacer used to form the measuring gas chamber is formed primarily of alumina. Also one of the two porous electrodes of the oxygen concentration cell element and one of the two porous electrodes of the oxygen pump element are exposed to the interior of the hollow measuring gas chamber. The measuring gas chamber is located at a forward end portion of the element section 51, and the detection portion 19 is where the measuring gas chamber is formed.

The heater 53 is formed such that a heat-generating resistor pattern formed primarily of Pt is sandwiched between insulating substrates formed primarily of alumina.

The element section 51 and the heater 53 are joined together via a ceramic layer (e.g., a zirconia ceramic or an alumina ceramic). A protection layer (not shown) which protects against poisoning is formed on the surface of the forward end portion of the detection element 5 at which the detection portion 19 is formed.

In the thus-configured detection element 5, the three electrode terminals 31, 32 and 33 are formed at a rear end portion (in FIG. 2, a right end portion) of the first plate surface 21, and the two electrode terminals 34 and 35 are formed at a rear end portion of the second plate surface 23.

The electrode terminals 31, 32 and 33 are formed on the element section 51, and one of the electrode terminals 31, 32 and 33 is electrically connected, for common use, to the one porous electrode of the oxygen concentration cell element which is exposed to the interior of the measuring gas chamber and to the one porous electrode of the oxygen pump element which is exposed to the interior of the measuring gas chamber. Also, the remaining two of the electrode terminals 31, 32 and 33 are electrically connected to the other porous electrode of the oxygen concentration cell element and the other porous electrode of the oxygen pump element, respectively.

The electrode terminals 34 and 35 are formed on the heater 53 and are connected to opposite ends, respectively, of the heat-generating resistor pattern through respective vias (not shown) extending through the heater 53 in the thickness direction of the heater 53.

Referring back to FIG. 1, the metallic shell 3 is a tubular member made of, for example, stainless steel and has a threaded portion 55 formed on its outer surface and a through hole 57 extending therethrough at its axial center. The metallic shell 3 also has a ledge 59 protruding radially inward in the through hole 57.

Furthermore, in the through hole 57 of the metallic shell 3, an annular holder (ceramic holder) 61 formed of, for example, alumina, annular powder filler layers (talc rings) 63 and 65, and an annular sleeve (ceramic sleeve) 67 formed of, for example, alumina are stacked in this order from the forward side to the rear side so as to surround the detection element 5 radially from the outside.

Also, a crimp packing 69 is disposed between the ceramic sleeve 67 and a rear end portion of the metallic shell 3, and a tubular metal holder 71 is disposed between the ceramic holder 61 and the ledge 59 of the metallic shell 3 for holding the talc ring 63 and the ceramic holder 61. The rear end portion of the metallic shell 3 is crimped so as to press the ceramic sleeve 67 forward through the crimp packing 69.

The protector 9 is a tubular member formed of, for example, stainless steel and is attached, by, for example, welding, to the outer circumference of a forward end portion of the metallic shell 3 so as to cover a protruding portion of the detection element 5. The protector 9 has a dual structure composed of an outer protector 9a and an inner protector 9b, and the outer and inner protectors 9a and 9b have a plurality of holes 9c formed in their respective side walls allowing for the passage of gas.

The ceramic separator 13 is a tubular member formed of, for example, alumina and is held in a rear portion of the tubular casing 11 by means of a tubular metal holding member 73 disposed in the rear portion of the tubular casing 11. That is, the ceramic separator 13 has an annular collar portion 74 protruding from its outer surface, and the collar portion 74 is supported by the metal holding member 73, whereby the ceramic separator 13 is held to the tubular casing 11.

The ceramic separator 13 has a through hole 75 extending therethrough in the axial direction and accommodates, in the through hole 75, a rear end portion of the detection element 5 (accordingly, the electrode terminals 31 to 35) and the connection terminals 41 to 45 electrically connected to the electrode terminals 31 to 35, respectively, as described below.

The closing member 15 is a grommet formed of, for example, fluororesin; is disposed at a rear end portion of the tubular casing 11; and is crimped from the outside, thereby being fixed to the tubular casing 11 (so as to be in contact with the rear end of the ceramic separator 13).

The lead wires 37 are connected to the rear ends of the connection terminals 41 to 45, respectively, (by crimping) and extend toward an external apparatus through respective through holes 77 formed in the closing member 15.

b) Next, the ceramic sleeve 67, which is an essential member of the first embodiment, will be described.

Figure 3A:
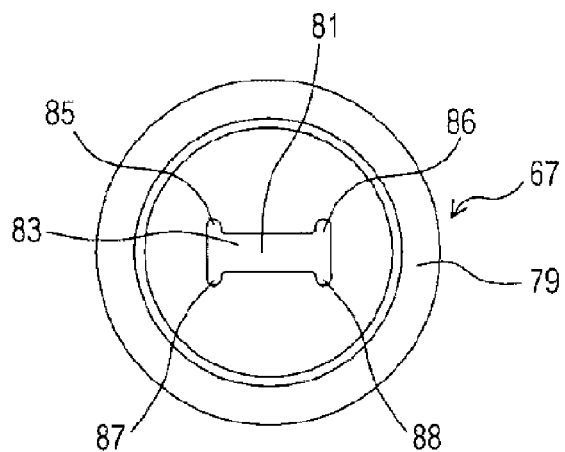
FIG. 3A is a plan view showing the rear end of a ceramic sleeve of the first embodiment.
Figure 3B:
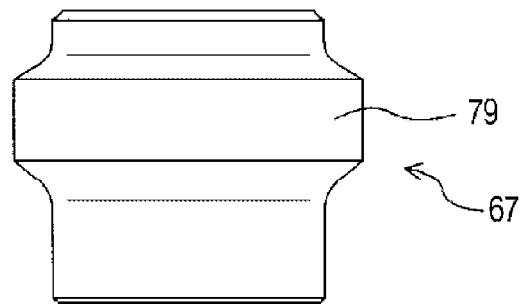
FIG. 3B is a front view of the ceramic sleeve of the first embodiment.
Figure 3C:
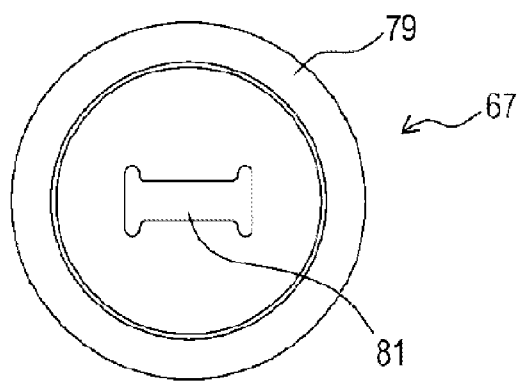
FIG. 3C is a bottom view showing the forward end of the ceramic sleeve of the first embodiment.

As shown in FIGS. 3A to 3C, the ceramic sleeve 67 is a cylindrical member; is disposed so as to surround the detection element 5 radially from the outside; and has a protrusion 79 protruding annularly outward from the outer circumference of its axially central portion.

The ceramic sleeve 67 has an element insertion hole 81 (through which the detection element 5 is inserted) formed at its axial center, having a substantially rectangular shape, and extending therethrough in the axial direction.

As viewed from the axial direction (see FIG. 3A), the element insertion hole 81 is composed of a main insertion hole 83 surrounded by four sides and having a rectangular shape (in the present embodiment, 1.8 mm vertical length× 4.8 mm horizontal length) and relief holes (first to fourth relief holes) 85, 86, 87 and 88, each surrounded by an outline which connects the ends of two adjacent sides of the four sides of the main insertion hole 83.

The element insertion hole 81 extends through the ceramic sleeve 67 from one side (front side shown in FIG. 3A) to the other side (back side shown in FIG. 3C) while the same cross-sectional shape is maintained. In the first embodiment, the relief holes 85, 86, 87 and 88 are provided for respective pairs each consisting of two adjacent sides of the four sides (i.e., provided at a total of four locations).

Figure 4:
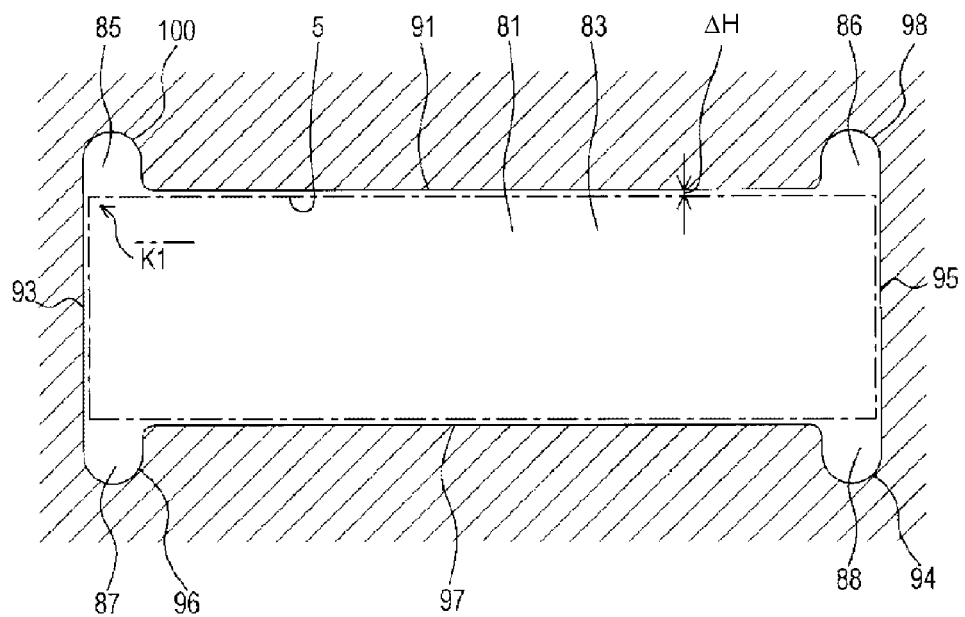
FIG. 4 is a plan view showing, on an enlarged scale, an element insertion hole of the ceramic sleeve of the first embodiment, where the ceramic region is hatched.

More specifically, as shown on an enlarged scale in FIG. 4, the main insertion hole 83 has a rectangular cross-sectional shape slightly greater than that of the detection element 5 so as to allow the insertion of the detection element 5 therethrough and to prevent play of the inserted detection element 5. For example, a slight clearance ΔH (in the first embodiment, 0.3 mm) is provided between the outer peripheral surface of the detection element 5 and the inner peripheral surface of the main insertion hole 83 over the entire periphery thereof.

The first relief hole 85 is surrounded by an outline 100 which connects the end of a first long side 91 (an upper long side in FIG. 4) and the end of a first short side 93 (a left-hand short side in FIG. 4) of the main insertion hole 83 and is provided radially outward of the main insertion hole 83. Furthermore, a portion of the outline 100 of the first relief hole 85 extends rectilinearly from the first short side 93.

Also, the second relief hole 86 is surrounded by an outline 98 which connects the end of the first long side 91 and the end of a second short side 95 (a right-hand short side in FIG. 4) of the main insertion hole 83 and is provided radially outward of the main insertion hole 83. Furthermore, a portion of the outline 98 of the second relief hole 86 extends rectilinearly from the second short side 95.

Furthermore, the third relief hole 87 is surrounded by an outline 96 which connects the end of a second long side 97 (a lower long side in FIG. 4) and the end of the first short side 93 of the main insertion hole 83 and is provided radially outward of the main insertion hole 83. Furthermore, a portion of the outline 96 of the third relief hole 87 extends rectilinearly from the first short side 93.

Also, the fourth relief hole 88 is surrounded by an outline 94 which connects the end of the second long side 97 and the end of the second short side 95 of the main insertion hole 83 and is provided radially outward of the main insertion hole 83. Furthermore, a portion of the outline 94 of the fourth relief hole 88 extends rectilinearly from the second short side 95.

Figure 5:
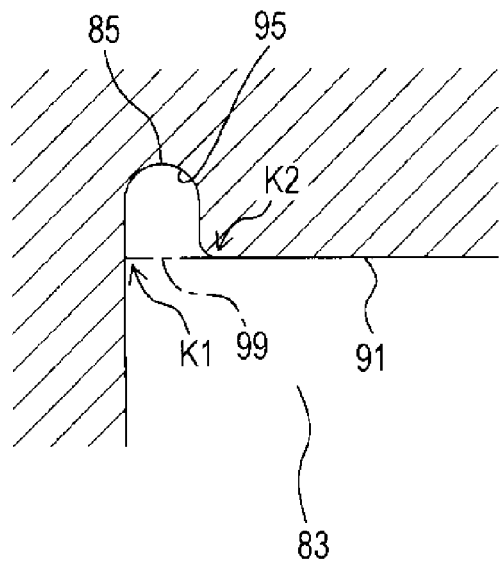
FIG. 5 is a plan view showing, on a further enlarged scale, a first relief hole of the ceramic sleeve of the first embodiment, where the ceramic region is hatched.

Furthermore, as shown on a further enlarged scale in FIG. 5, the first relief hole 85 is formed in the vicinity of an intersection K1 of the first short side 93 and an extension line (i.e., the outline of the main insertion hole 83) 99 of the first long side 91 so as to protrude toward a side opposite the main insertion hole 83 (toward the upper side in FIG. 5) with respect to the extension line 99.

The first relief hole 85 is formed from the main insertion hole 83 along the extending direction of the first short side 93 and has a width of 0.6 mm×a depth of 0.6 mm, and its depth portion is smoothly curved along a circle having a radius of 0.3 mm. An edge K2 defined by the first long side 91 and the outline 100 of the first relief hole 85 is smoothly curved or radiused at a radius of, for example, 0.1 mm.

That is, the first relief hole 85 provided in communication with the main insertion hole 83 is formed as follows: an end of one side (first short side 93) reaches the intersection K1 with the extension line 99 of the other side (first long side 91), whereas an end of the first long side 91 does not reach the intersection K1; and the outline 100 of the first relief hole 85 is formed smoothly; i.e., formed without an edge (an angular profile), from the end of the first short side 93 to the end of the first long side 91.

As shown in FIG. 4, the remaining second to fourth relief holes 86 to 88 have respective shapes similar to (shapes symmetrical to) those of the first relief hole 85; therefore, the relief holes 86 to 88 are briefly described below.

The second relief hole 86 is formed symmetrical to the first relief hole 85 with respect to the horizontal direction of FIG. 4; the third relief hole 87 is formed symmetrical to the first relief hole 85 in the vertical direction of FIG. 4; and the fourth relief hole 88 is formed symmetrical to the second relief hole 86 with respect to the vertical direction of FIG. 4.

c) Next, the ceramic holder 61, which is an essential member of the first embodiment, will be described.

Figure 6A:
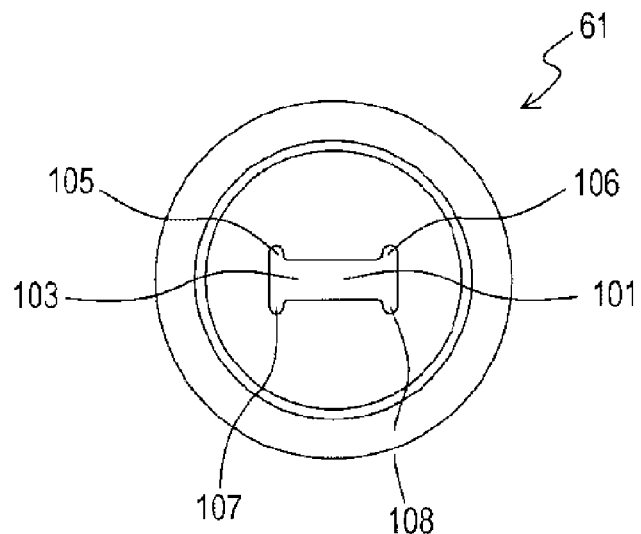
FIG. 6A is a plan view showing the rear end of a ceramic holder of the first embodiment.
Figure 6B:
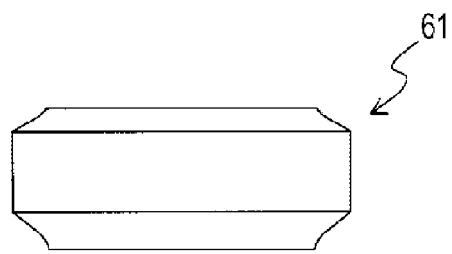
FIG. 6B is a front view of the ceramic holder of the first embodiment.
Figure 6C:
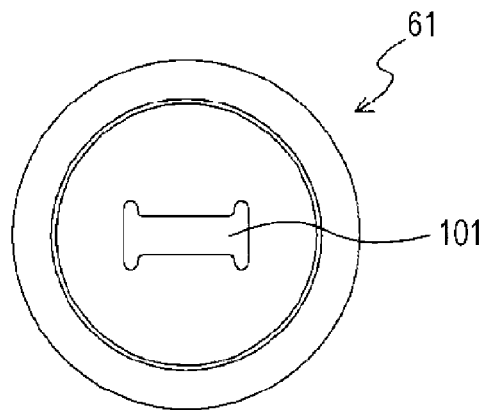
FIG. 6C is a bottom view showing the forward end of the ceramic holder of the first embodiment.

As shown in FIGS. 6A to 6C, the ceramic holder 61 also has an element insertion hole 101 (through which the detection element 5 is inserted). The element insertion hole 101 has a configuration (shape) similar to that of the ceramic sleeve 67; thus, the ceramic holder 61 is described briefly.

As shown in FIGS. 6A to 6C, the ceramic holder 61 is a tubular member; is disposed so as to surround the detection element 5 radially from the outside; and has, similar to the ceramic sleeve 67, an element insertion hole 101 extending therethrough in the axial direction. The ceramic holder 61 is shorter in axial length than the ceramic sleeve 67 and has a substantially platelike form (disklike shape).

As viewed from the axial direction (see FIG. 6A), the element insertion hole 101 is composed of a main insertion hole 103 having a rectangular shape similar to that of the main insertion hole of the ceramic sleeve 67 and relief holes (first to fourth relief holes) 105, 106, 107 and 108, each surrounded by an outline which connects the ends of two adjacent sides of the four sides of the main insertion hole 103, and having a shape similar to that of a relief hole of the ceramic sleeve 67.

d) Next, the ceramic separator 13, which is an essential member of the first embodiment, will be described.

Figure 7:
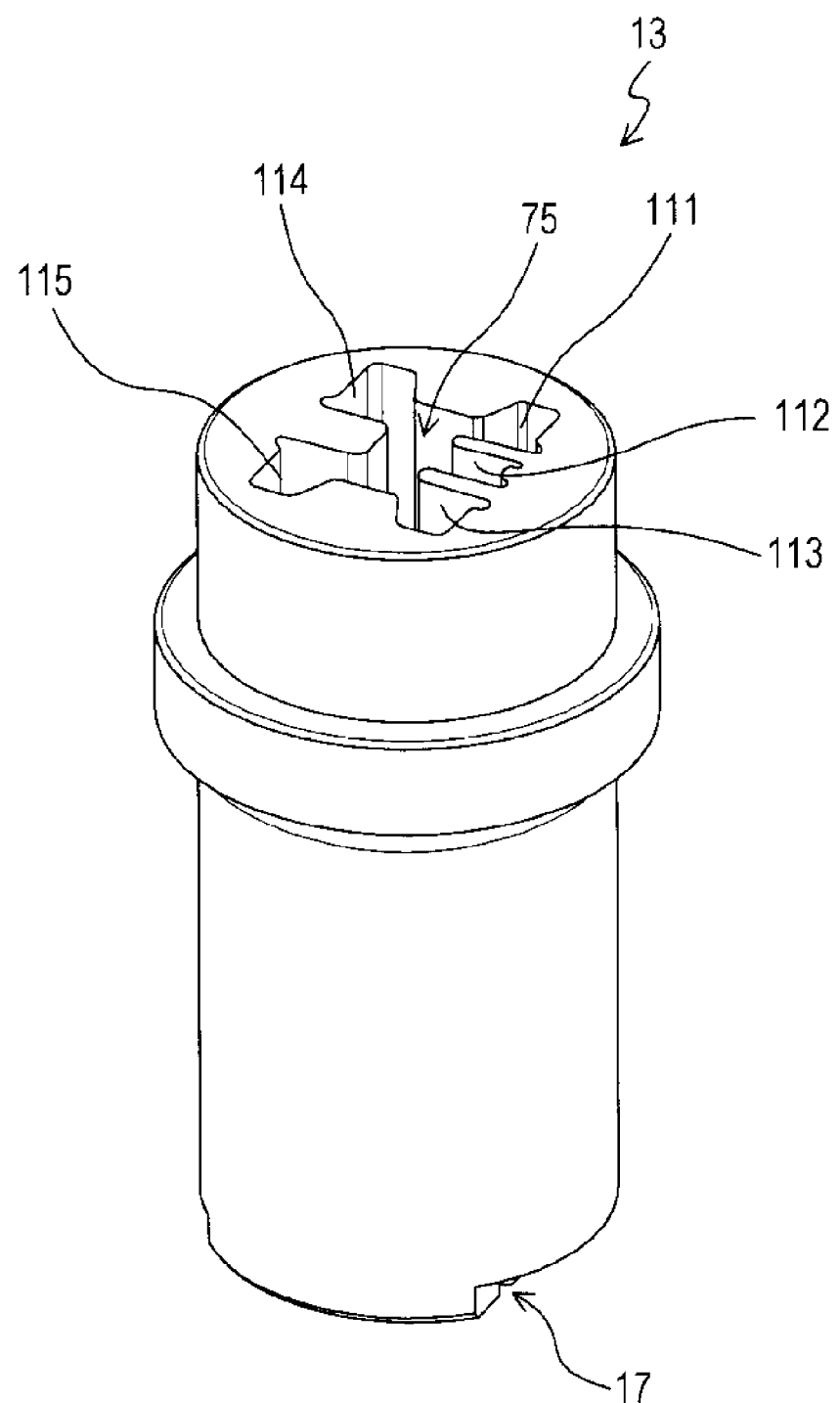
FIG. 7 is a perspective view showing a ceramic separator of the first embodiment in which its rear end surface is visible.
Figure 8:
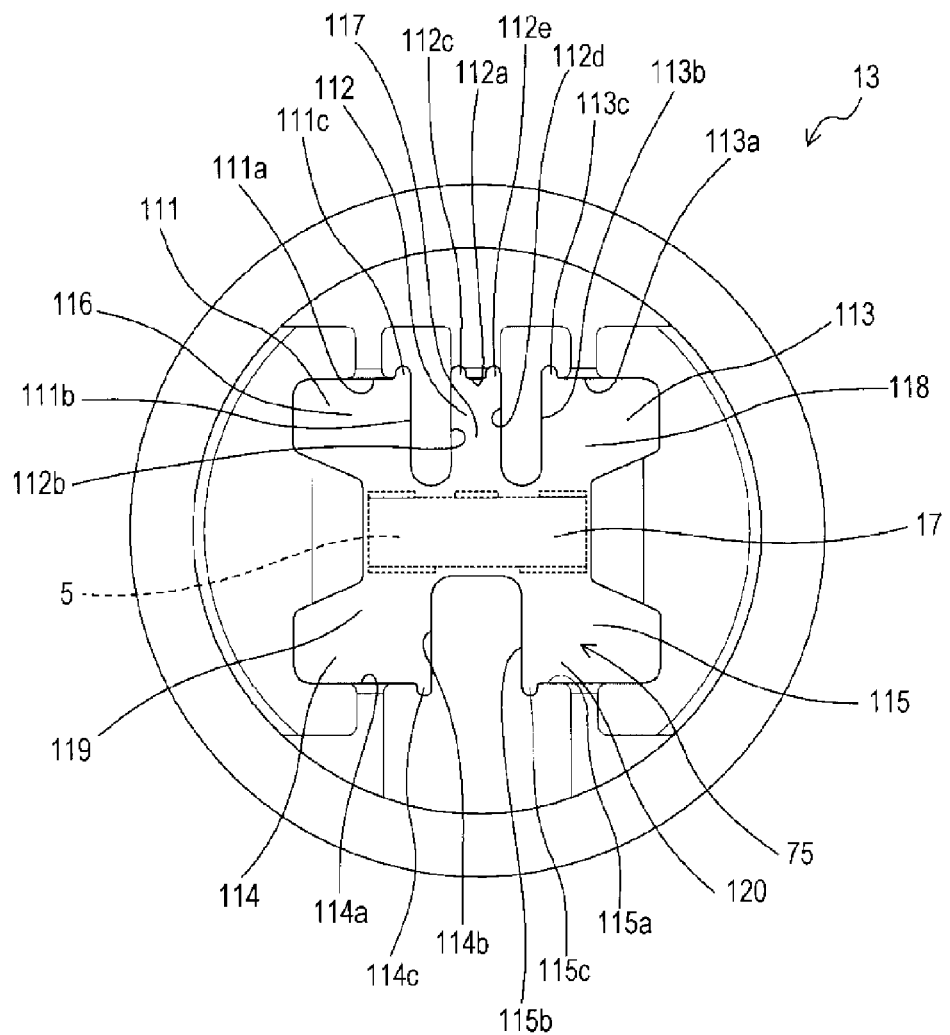
FIG. 8 is a plan view of the ceramic separator of the first embodiment viewed from the rear side, showing a state in which connection terminals are not disposed therein.

As shown in FIGS. 7 and 8, the ceramic separator 13 has five terminal insertion holes (first to fifth terminal insertion holes) 111, 112, 113, 114 and 115 into which five connection terminals 41 to 45 are inserted respectively along the axial direction, and an element insertion hole 17 which communicates with the five terminal insertion holes 111 to 115 and into which a rear end portion of the detection element 5 is inserted. The terminal insertion holes 111 to 115 and the element insertion hole 17 collectively constitute the through hole 75 extending through the ceramic separator 13 in the axial direction.

Specifically, as shown in FIG. 8, as viewed from the axial direction (a direction perpendicular to the paper on which FIG. 8 appears), the ceramic separator 13 has a first terminal insertion hole 111 which has a substantially pentagonal shape and into which the first connection terminal 41 is inserted; a second terminal insertion hole 112 which has a substantially rectangular shape and into which the second connection terminal 42 is inserted; a third terminal insertion hole 113 which has a substantially pentagonal shape and into which the third connection terminal 43 is inserted; a fourth terminal insertion hole 114 which has a substantially pentagonal shape and into which the fourth connection terminal 44 is inserted; and a fifth terminal insertion hole 115 which has a substantially pentagonal shape and into which the fifth connection terminal 45 is inserted. The terminal insertion holes 111 to 115 communicate with the element insertion hole 17 at respective sides thereof facing the center of the ceramic separator 13.

Furthermore, in the first embodiment, the first terminal insertion hole 111 has a first main insertion hole 116 having a substantially pentagonal shape and a first relief hole 111c which is surrounded by an outline connecting the end of an upper side 111a and the end of a right side 111b of the first main insertion hole 116. The first terminal insertion hold 111 is located radially outward of the first main insertion hole 116 and has a shape similar to that of the second relief hole 86 of the ceramic sleeve 67.

The second terminal insertion hole 112 has a second main insertion hole 117 having a substantially rectangular shape; a second relief hole 112c which is surrounded by an outline connecting the end of an upper side 112a and the end of a left side 112b of the second main insertion hole 117 and is located radially outward of the second main insertion hole 117 and which has a shape similar to that of the first relief hole 85 of the ceramic sleeve 67; and a third relief hole 112e which is surrounded by an outline connecting the end of the upper side 112a and the end of a right side 112d and is located radially outward of the second main insertion hole 117 and which has a shape similar to that of the second relief hole 86 of the ceramic sleeve 67.

The third terminal insertion hole 113 has a third main insertion hole 118 having a substantially pentagonal shape and a fourth relief hole 113c which is surrounded by an outline connecting the end of an upper side 113a and the end of a left side 113b of the third main insertion hole 118 and is located radially outward of the third main insertion hole 118 and which has a shape similar to that of the first relief hole 85 of the ceramic sleeve 67.

The fourth terminal insertion hole 114 has a fourth main insertion hole 119 having a substantially pentagonal shape and a fifth relief hole 114c which is surrounded by an outline connecting the end of a lower side 114a and the end of a right side 114b of the fourth main insertion hole 119 and is located radially outward of the fourth main insertion hole 119 and which has a shape similar to that of the fourth relief hole 88 of the ceramic sleeve 67.

The fifth terminal insertion hole 115 has a fifth main insertion hole 120 having a substantially pentagonal shape and a sixth relief hole 115c which is surrounded by an outline connecting the end of a lower side 115a and the end of a left side 115b of the fifth main insertion hole 120 and is located radially outward of the fifth main insertion hole 120 and which has a shape similar to that of the third relief hole 87 of the ceramic sleeve 67.

Next, the shapes of the connection terminals 41 to 45 to be inserted into the terminal insertion holes 111 to 115, respectively, will be described. Since the terminal insertion holes 111 to 115 have shapes corresponding to external shapes of the connection terminals 41 to 45, respectively, the shapes of the connection terminals 41 to 45 will be described. A second embodiment described below also uses the connection terminals 41 to 45 used in the first embodiment.

Figure 9:
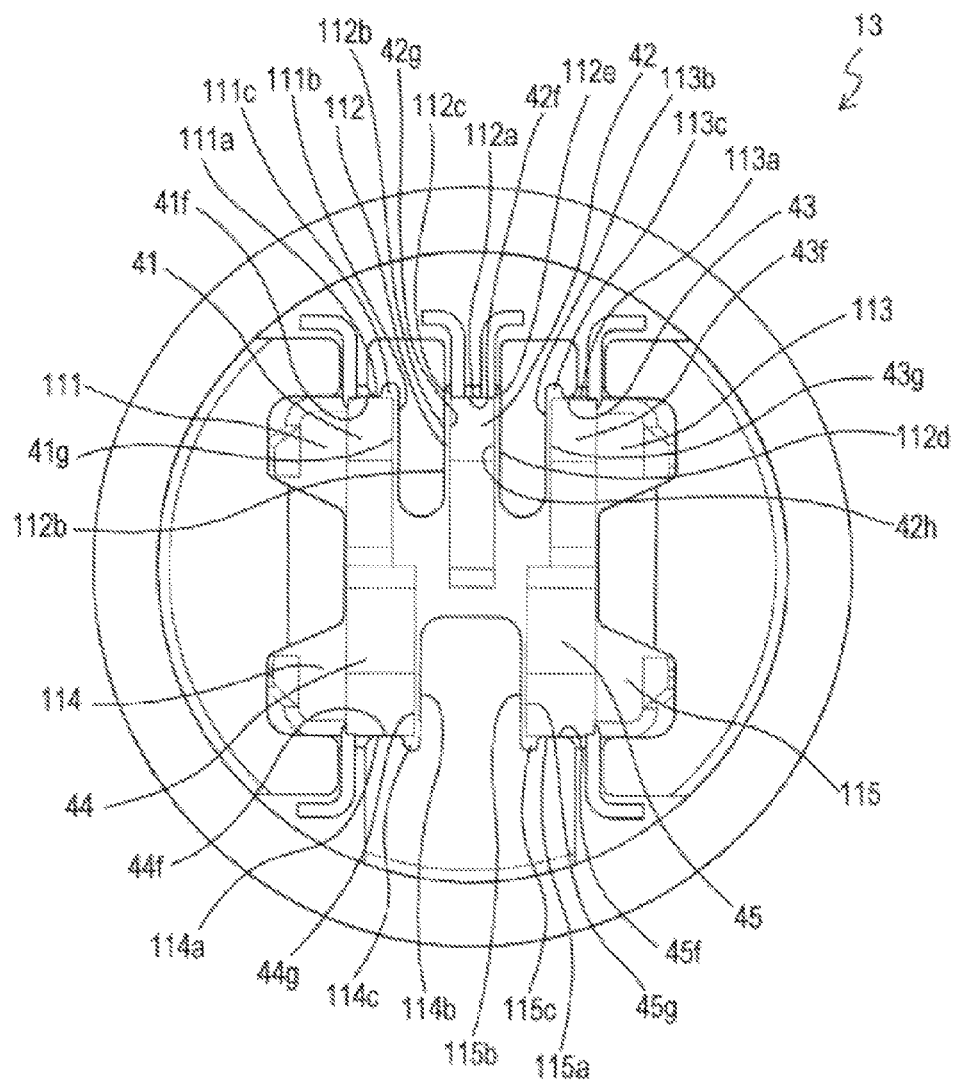
FIG. 9 is a plan view of the ceramic separator of the first embodiment viewed from the rear side, showing a state in which the connection terminals are disposed therein.

As shown in FIG. 9, the elongated first connection terminal 41 extending in the axial direction of the ceramic separator 13 (a direction perpendicular to the paper on which FIG. 9 appears) is disposed in the first terminal insertion hole 111. The elongated second connection terminal 42 extending in the axial direction of the ceramic separator 13 is disposed in the second terminal insertion hole 112. The elongated third connection terminal 43 extending in the axial direction of the ceramic separator 13 is disposed in the third terminal insertion hole 113. The elongated fourth connection terminal 44 extending in the axial direction of the ceramic separator 13 is disposed in the fourth terminal insertion hole 114. The elongated fifth connection terminal 45 extending in the axial direction of the ceramic separator 13 is disposed in the fifth terminal insertion hole 115.

Figure 10A:
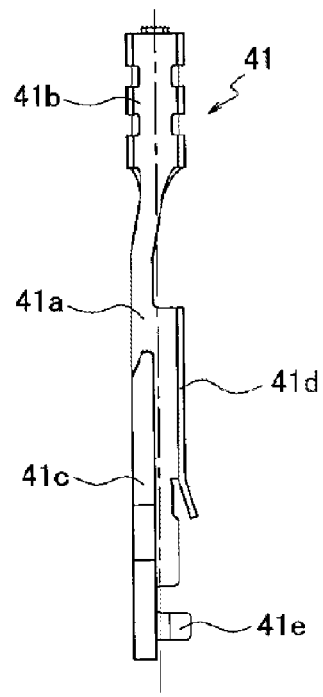
FIG. 10A is a front view showing a first connection terminal.
Figure 10B:
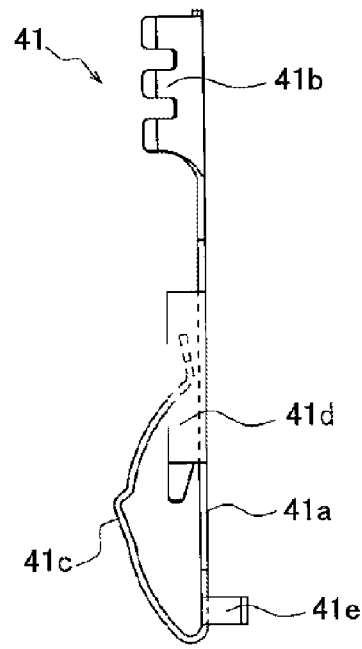
FIG. 10B is a side view showing the first connection terminal.

As shown in FIGS. 10A and 10B, the first connection terminal 41 has an elongated central portion 41a; a lead wire crimp portion 41b located rearward (upward in FIGS. 10A and 10B) of the central portion 41a and adapted to be crimped to the metal core wire 37a of the lead wire 37; a curved portion 41c curved like a bow from the forward end toward the rear end of the central portion 41a; a side portion 41d provided along one side edge (the right side edge in FIG. 10A) of the central portion 41a and bent perpendicularly to the central portion 41a toward the curved portion 41c (leftward in FIG. 10B); and a forward end tab 41e bent at a forward end portion of the central portion 41a in a direction opposite the side portion 41d and further bent perpendicularly outward (rightward in FIG. 10A) at its distal end.

Figure 10C:
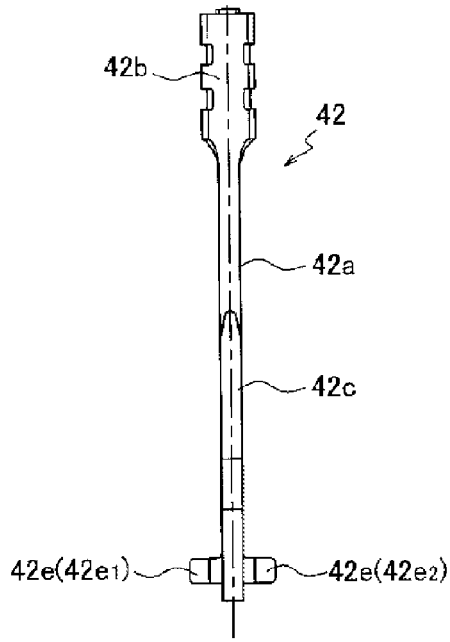
FIG. 10C is a front view showing a second connection terminal.
Figure 10D:
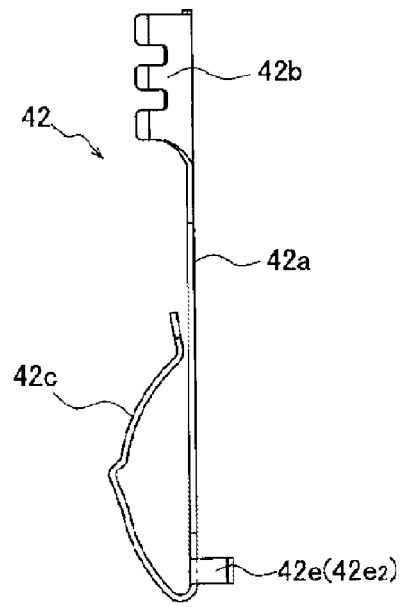
FIG. 10D is a side view showing the second connection terminal.

As shown in FIGS. 10C and 10D, the second connection terminal 42 has an elongated central portion 42a; a lead wire crimp portion 42b located rearward (upward in FIGS. 10C and 10D) of the central portion 42a and adapted to be crimped to the metal core wire 37a of the lead wire 37; a curved portion 42c curved like a bow from the forward end toward the rear end of the central portion 42a; and left and right forward end tabs 42e (42e1 and 42e2) bent at opposite sides of a forward end portion of the central portion 42a in a direction opposite the curved portion 42c (rightward in FIG. 10D) and further bent perpendicularly outward (leftward and rightward in FIG. 10C) at their distal ends.

The third connection terminal 43 has a shape basically similar to that of the first connection terminal 41. Specifically, the third connection terminal 43 has portions which correspond to the side portion 41*d*, the forward end tab 41*e*, etc., of the first connection terminal 41 and which are mirror images thereof (with respect to the horizontal direction of FIG. 9). Thus, a detailed description thereof is omitted.

The fourth connection terminal 44 has a shape basically similar to that of the second connection terminal 42 except that its width is slightly greater. Thus, a detailed description thereof is omitted.

Similarly, the fifth connection terminal 45 has a shape basically similar to that of the first connection terminal 41 except that its width is slightly greater. Thus, a detailed description thereof is omitted.

In the first embodiment, as shown in FIG. 9, as viewed from the axial direction of the ceramic separator 13, the connection terminals 41 to 45 described above are configured such that their edges do not come into contact with inner peripheral surfaces of the terminal insertion holes 111 to 115, respectively.

Specifically, as shown in FIG. 9, by virtue of the first relief hole 111*c*, an edge formed by an upper end 41*f* and a right end 41*g* of the first connection terminal 41 does not contact an inner peripheral surface of the first terminal insertion hole 111.

Also, by virtue of the second relief hole 112*c*, an edge formed by an upper end 42*f* and a left end 42*g* of the second connection terminal 42 does not contact an inner peripheral surface of the second terminal insertion hole 112. By virtue of the third relief hole 112*e*, an edge formed by the upper end 42*f* and a right end 42*h* of the second connection terminal 42 does not contact an inner peripheral surface of the second terminal insertion hole 112.

Also, by virtue of the fourth relief hole 113*c*, an edge formed by an upper end 43*f* and a left end 43*g* of the third connection terminal 43 does not contact an inner peripheral surface of the third terminal insertion hole 113.

Also, by virtue of the fifth relief hole 114*c*, an edge formed by a lower end 44*f* and a right end 44*g* of the fourth connection terminal 44 does not contact an inner peripheral surface of the fourth terminal insertion hole 114.

Furthermore, by virtue of the sixth relief hole 115*c*, an edge formed by a lower end 45*f* and a left end 45*g* of the fifth connection terminal 45 does not contact an inner peripheral surface of the fifth terminal insertion hole 115.

e) Next, the effects of the first embodiment will be described.

In the first embodiment, the element insertion hole 81 of the ceramic sleeve 67 has first to fourth relief holes 85 to 88 formed at four corners, respectively, of the main insertion hole 83 having a quadrate cross section, and the element insertion hole 101 of the ceramic holder 61 has first to fourth relief holes 105 to 108 formed at four corners, respectively, of the main insertion hole 103 having a quadrate cross section.

The main insertion holes 83 and 103 do not have radiused edges. Therefore, the dimensions of the detection element 5 to be inserted into the main insertion holes 83 and 103 can be substantially equal to the dimensions of the main insertion holes 83 and 103. As a result, a clearance between a side surface of the detection element 5 and corresponding inner peripheral surfaces of the element insertion holes 81 and 101 can be small, thereby preventing play of the detection element 5 within the element insertion holes 81 and 101.

Of the two sides of each of the main insertion holes 83 and 103 connected to each of the outlines of the relief holes 85 to 88 and 105 to 108, one side reaches an intersection with an extension line of the other side. Thus, the inner peripheral surface of each of the main insertion holes 83 and 103 which includes the one side can face a corresponding side surface of the detection element 5 over substantially the entire of the side surface, thereby further reducing play of the detection element 5 within the element insertion holes 81 and 101.

In the first embodiment, the first to fifth terminal insertion holes 111 to 115 of the ceramic separator 13 have first to sixth relief holes 111*c*, 112*c*, 112*e*, 113*c*, 114*c* and 115*c* at edges (corners) of the first to fifth main insertion holes 116 to 120, respectively.

The first to fifth main insertion holes 116 to 120 do not have radiused edges. Therefore, the dimensions of the first to fifth connection terminals 41 to 45 to be inserted into the first to fifth main insertion holes 116 to 120, respectively, can be substantially equal to the dimensions of the first to fifth main insertion holes 116 to 120. As a result, a clearance between side surfaces of the first to fifth connection terminals 41 to 45 and corresponding inner peripheral surfaces of the first to fifth terminal insertion holes 111 to 115 can be small, thereby preventing play of the first to fifth connection terminals 41 to 45 within the first to fifth terminal insertion holes 111 to 115, respectively.

Of the two sides of each of the first to fifth main insertion holes 116 to 120 connected to each of the outlines of the first to sixth relief holes 111*c* to 115*c*, one side reaches an intersection with an extension line of the other side. Thus, the inner peripheral surface of each of the first to fifth main insertion holes 116 to 120 which includes the one side can face a corresponding side surface of each of the first to fifth connection terminals 41 to 45 over substantially the entire range. Therefore, the play of the first to fifth connection terminals 41 to 45 within the first to fifth insertion holes 111 to 115, respectively, can be further reduced.

Furthermore, the first embodiment has the following advantage: since each of the outlines of the relief holes 85 to 108, 105 to 108, 111*c*, 112*c*, 112*e*, 113*c*, 114*c* and 115*c* is formed smoothly from the end of the one side to the end of the other side, cracks are further unlikely to generate in the ceramic members.

Second Embodiment

An air/fuel ratio sensor 1A of the second embodiment will next be described. The air/fuel ratio sensor 1A of the second embodiment differs from the air/fuel ratio sensor 1 of the first embodiment in the configurations of a ceramic sleeve 67A, a ceramic holder 61A and a ceramic separator 13A. Thus, the configurations of the ceramic sleeve 67A, the ceramic holder 61A and the ceramic separator 13A of the air/fuel ratio sensor 1A of the second embodiment are described in detail, and a description of the configurations of other common members (e.g., the detection element 5 and the metallic shell 3) is omitted.

f) First, the ceramic sleeve 67A, which is an essential member of the second embodiment, will be described.

Figure 11A:
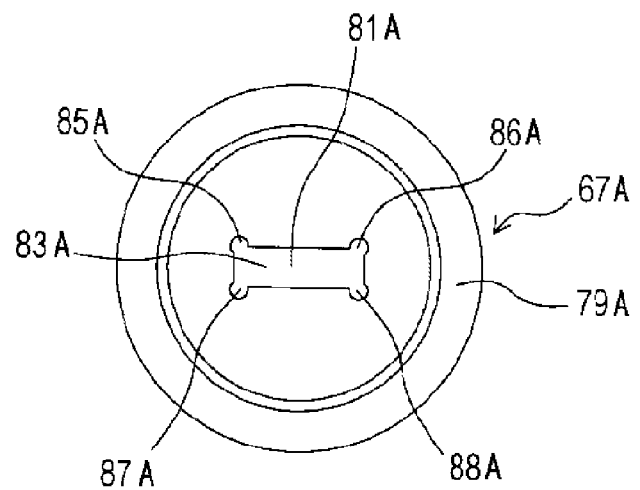
FIG. 11A is a plan view showing the rear end of a ceramic sleeve of a second embodiment.
Figure 11B:
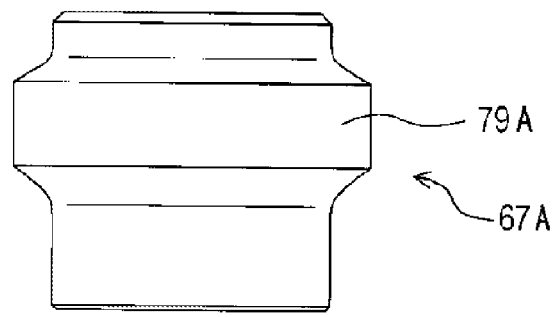
FIG. 11B is a front view of the ceramic sleeve of the second embodiment.
Figure 11C:
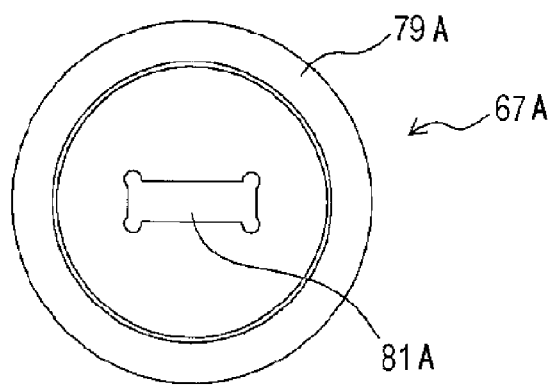
FIG. 11C is a bottom view showing the forward end of the ceramic sleeve of the second embodiment.

As shown in FIGS. 11A to 11C, the ceramic sleeve 67A is a cylindrical member; is disposed so as to surround the detection element 5 radially from the outside; and has a protrusion 79A protruding annularly outward from the outer circumference of its axially central portion.

In the second embodiment, the ceramic sleeve 67A has an element insertion hole 81A (through which the detection element 5 is inserted) formed at its axial center, having a substantially rectangular shape, and extending therethrough in the axial direction.

As viewed from the axial direction (see FIG. 11A), the element insertion hole 81A is composed of a main insertion hole 83A surrounded by four sides and having a quadrate shape (in the present embodiment, for example, 1.8 mm vertical length×4.8 mm horizontal length) and relief holes (first to fourth relief holes) 85A, 86A, 87A and 88A, each surrounded by an outline which connects the ends of two adjacent sides of the four sides of the main insertion hole 83A. The element insertion hole 81A extends through the ceramic sleeve 67A from one side (front side shown in FIG. 11A) to the other side (back side shown in FIG. 11C) while the same cross-sectional shape is maintained. In the present embodiment, the relief holes are provided for respective pairs each consisting of two adjacent sides of the four sides (i.e., provided at a total of four locations).

Figure 12:
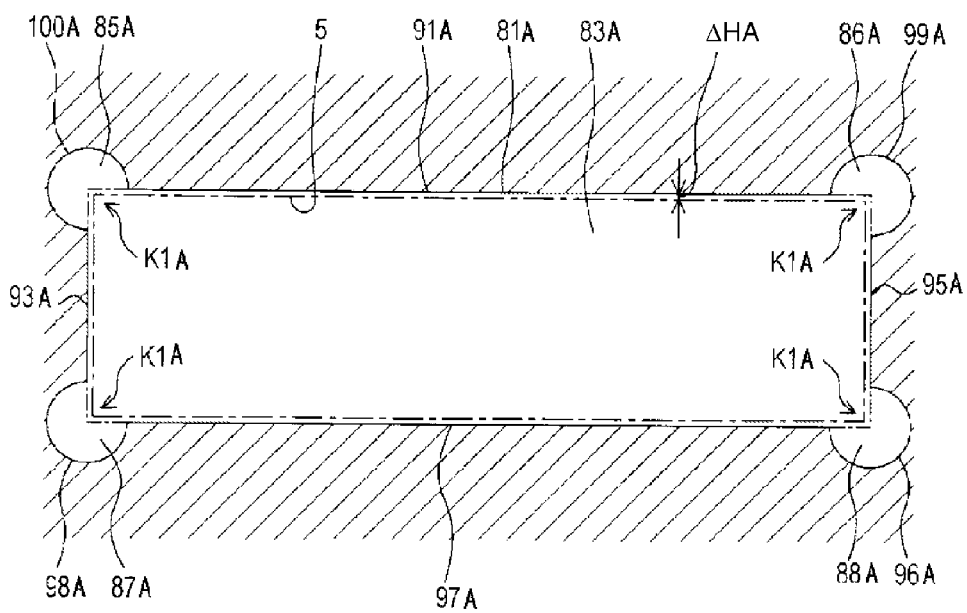
FIG. 12 is a plan view showing, on an enlarged scale, an element insertion hole of the ceramic sleeve of the second embodiment, where the ceramic region is hatched.

More specifically, as shown on an enlarged scale in FIG. 12, the main insertion hole 83A has a rectangular cross-sectional shape slightly greater than that of the detection element 5 so as to allow insertion of the detection element 5 therethrough and to prevent play of the inserted detection element 5. For example, a slight clearance ΔHA (in the second embodiment, 0.3 mm) is provided between the outer peripheral surface of the detection element 5 and the inner peripheral surface of the main insertion hole 83A over the entire periphery thereof.

The first relief hole 85A is surrounded by an outline 100A which connects the end of a first long side 91A (an upper long side in FIG. 12) and the end of a first short side 93A (a left-hand short side in FIG. 12) of the main insertion hole 83A and is provided radially outward of the main insertion hole 83A. Also, the second relief hole 86A is surrounded by an outline 99A which connects the end of the first long side 91A and the end of a second short side 95A (a right-hand short side in FIG. 12) of the main insertion hole 83A and is provided radially outward of the main insertion hole 83A.

Also, the third relief hole 87A is surrounded by an outline 98A which connects the end of a second long side 97A (a lower long side in FIG. 12) and the end of the first short side 93A of the main insertion hole 83A and is provided radially outward of the main insertion hole 83A.

Also, the fourth relief hole 88A is surrounded by an outline 96A which connects the end of the second long side 97A and the end of the second short side 95A of the main insertion hole 83A and is provided radially outward of the main insertion hole 83A.

Figure 13:
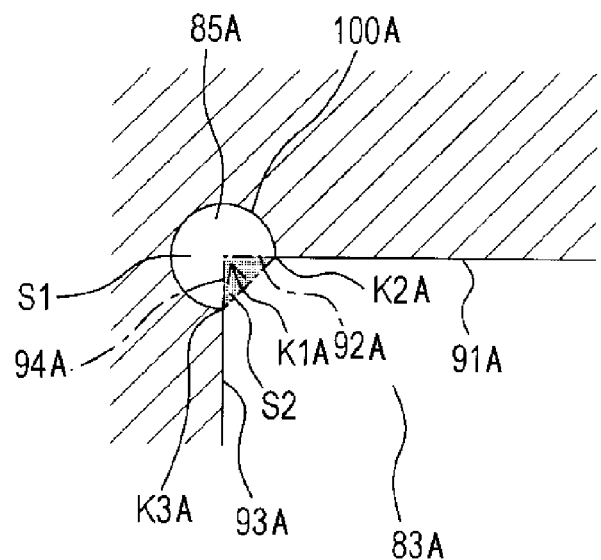
FIG. 13 is a plan view showing, on a further enlarged scale, a first relief hole of the ceramic sleeve of the second embodiment, where the ceramic region is hatched.

Furthermore, as shown on a further enlarged scale in FIG. 13, the first relief hole 85A is formed in the vicinity of an intersection K1A of an extension line (i.e., a portion of the outline of the main insertion hole 83A) 92A of the first long side 91A and an extension line (i.e., a portion of the outline of the main insertion hole 83A) 94A of the first short side 93A so as to protrude radially outward of the main insertion hole 83A with respect to the extension lines 92A and 94A.

The shape (outline) 100A of the first relief hole 85A is an arc having a radius of 0.3 mm and a center at the intersection K1A of the extension line 92A of the first long side 91A and the extension line 94A of the first short side 93A.

That is, the outline 100A of the first relief hole 85A ranges from an intersection K2A of the first long side 91A and a circle having a center at the intersection K1A to an intersection K3A of the circle and the first short side 93A. Therefore, an area S1 of the first relief hole 85A is the area of a region obtained by removing a portion of the main insertion hole 83A from the circle having a radius of 0.3 mm; i.e., the area of the ¾ circle.

Furthermore, in the present embodiment, the area S1 of the first relief hole 85A is greater than an area S2 of a triangle (a shaded region in FIG. 13) defined by the intersections K1A, K2A and K3A.

In the present invention, the location of the center of the circle is not particularly limited so long as the magnitude relationship requirement between the area S1 of the first relief hole 85A and the area S2 of the triangle (S1>S2) and the relational requirement that the outline 100A of the first relief hole 85A intersect with the first long side 91A and the first short side 93A are satisfied; furthermore, the outline 100A does not need to have a circular shape (i.e., no particular limitation is imposed on the shape) so long as the above two requirements are satisfied.

As shown in FIG. 12, since the second to fourth relief holes 86A to 88A have an arc shape (provided that the shape must be symmetrical); specifically, a ¾ circle, similar to that of the first relief hole 85A, a detailed description thereof is omitted.

That is, the second relief hole 86A has a shape which is a mirror image of the shape of the first relief hole 85A with respect to the horizontal direction of FIG. 12; the third relief hole 87A has a shape which is a mirror image of the shape of the first relief hole 85A with respect to the vertical direction of FIG. 12; and the fourth relief hole 88A has a shape which is a mirror image of the shape of the second relief hole 86A with respect to the vertical direction of FIG. 12.

g) Next, the ceramic holder 61A, which is an essential member of the second embodiment will be described.

Figure 14A:
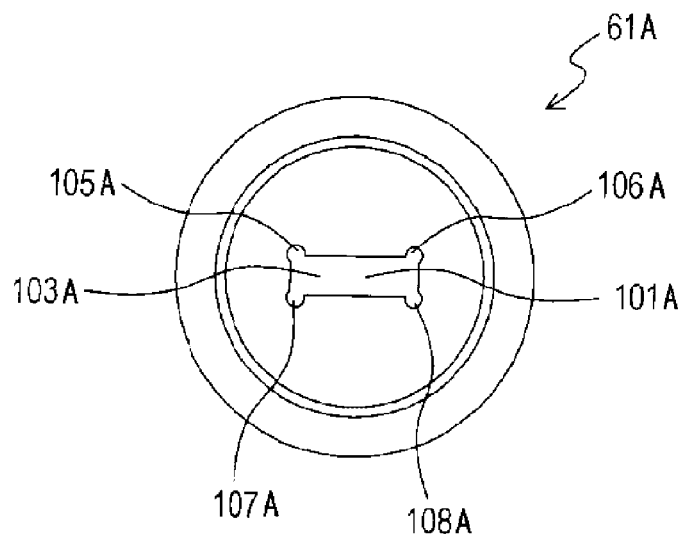
FIG. 14A is a plan view showing the rear end of a ceramic holder of the second embodiment.
Figure 14B:
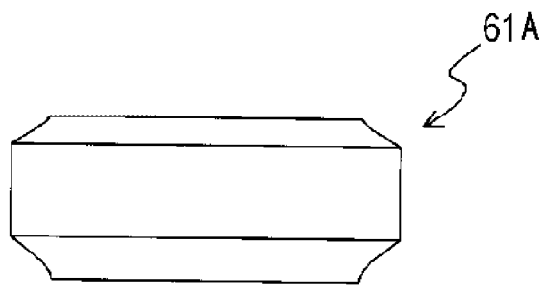
FIG. 14B is a front view of the ceramic holder of the second embodiment.
Figure 14C:
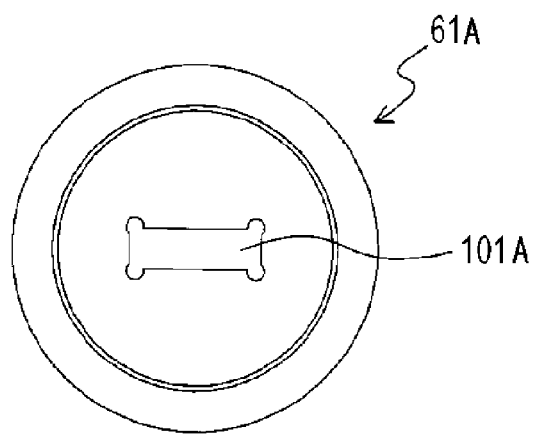
FIG. 14C is a bottom view showing the forward end of the ceramic holder of the second embodiment.

As shown in FIGS. 14A to 14C, the ceramic holder 61A also has an element insertion hole 101A (through which the detection element 5 is inserted). The element insertion hole 101A has a configuration (shape) similar to that of the ceramic sleeve 67A. Thus, the ceramic holder 61A is described briefly.

As shown in FIGS. 14A to 14C, the ceramic holder 61A is a tubular member; is disposed so as to surround the detection element 5 radially from the outside; and has, similar to the ceramic sleeve 67A, an element insertion hole 101A having a substantially rectangular shape and extending therethrough in the axial direction. The ceramic holder 61A is shorter in axial length than the ceramic sleeve 67A and has a substantially platelike form (disklike shape).

As viewed from the axial direction (see FIG. 14A), the element insertion hole 101A is composed of a main insertion hole 103A having a quadrate (rectangular) shape similar to that of the main insertion hole of the ceramic sleeve 67A and relief holes (first to fourth relief holes) 105A, 106A, 107A and 108A, each surrounded by an outline which connects the ends of two adjacent sides of the four sides of the main insertion hole 103A, and having a shape (an arc shape of a ¾ circle) similar to that of a relief hole of the ceramic sleeve 67A.

h) Next, the ceramic separator 13A, which is an essential member of the second embodiment will be described.

Figure 15:
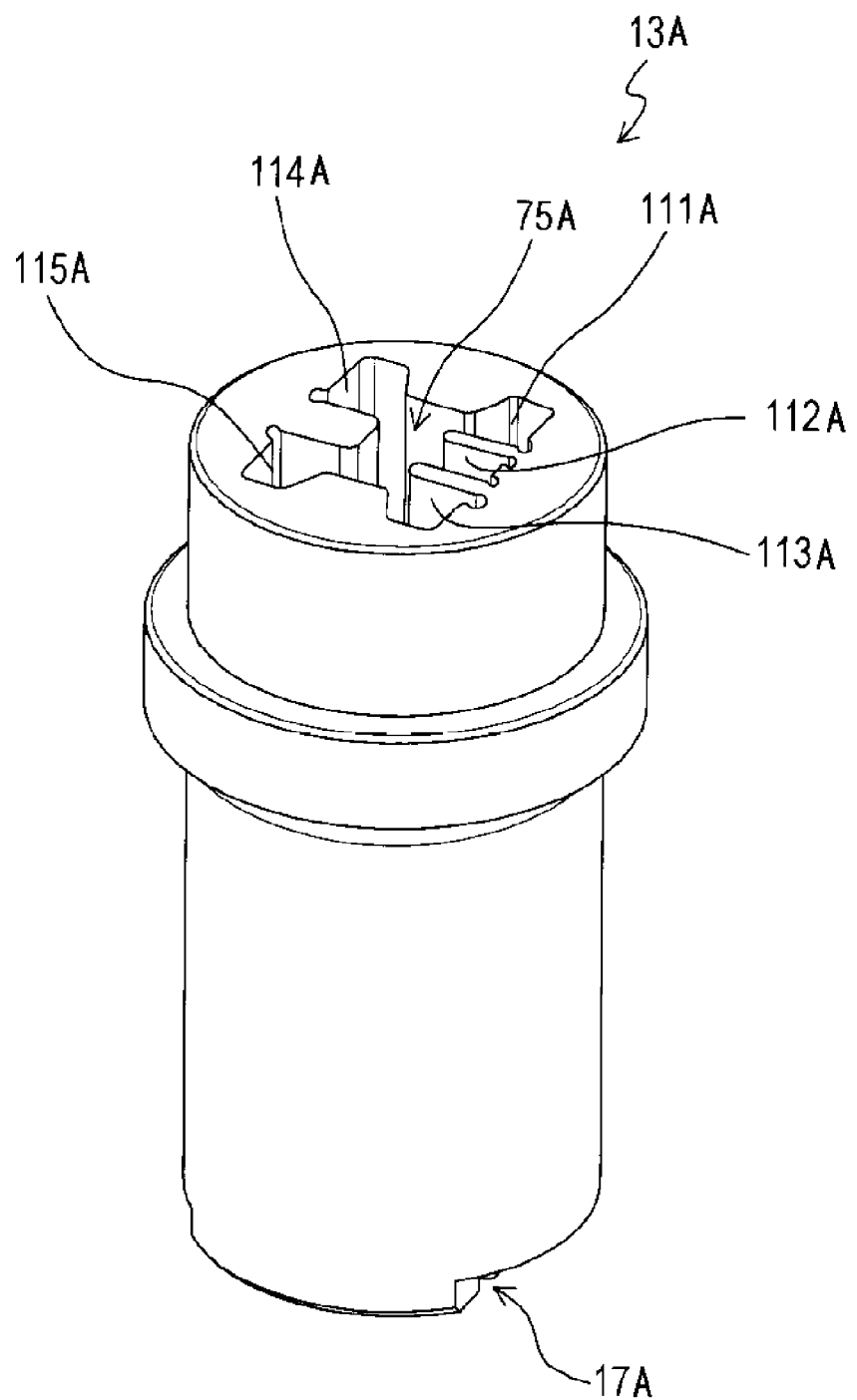
FIG. 15 is a perspective view showing a ceramic separator of the second embodiment in which its rear end surface is visible.
Figure 16:
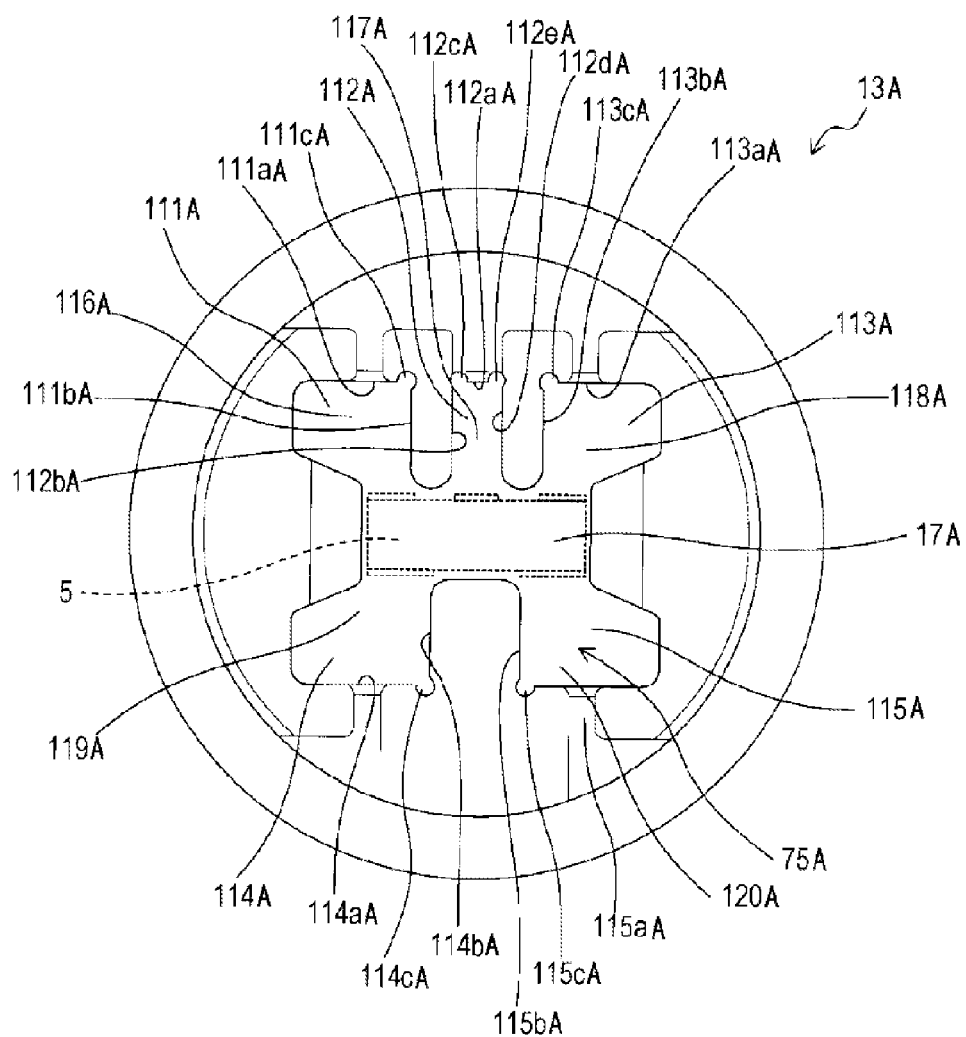
FIG. 16 is a plan view of the ceramic separator of the second embodiment viewed from the rear side, showing a state in which connection terminals are not disposed therein.

As shown in FIGS. 15 and 16, the ceramic separator 13A has five terminal insertion holes (first to fifth terminal insertion holes) 111A, 112A, 113A, 114A and 115A into which five connection terminals 41 to 45 are inserted respectively along the axial direction, and an element insertion hole 17A into which a rear end portion of the detection element 5 is inserted. The first to fifth terminal insertion holes 111A to 115A and the element insertion hole 17A collectively constitute a through hole 75A extending through the ceramic separator 13A in the axial direction.

Specifically, as shown in FIG. 16, as viewed from the axial direction (a direction perpendicular to the paper on which FIG. 16 appears), the ceramic separator 13A has a first terminal insertion hole 111A which has a substantially pentagonal shape and into which the first connection terminal 41 is inserted; a second terminal insertion hole 112A which has a substantially rectangular shape and into which the second connection terminal 42 is inserted; a third terminal insertion hole 113A which has a substantially pentagonal shape and into which the third connection terminal 43 is inserted; a fourth terminal insertion hole 114A which has a substantially pentagonal shape and into which the fourth connection terminal 44 is inserted; and a fifth terminal insertion hole 115A which has a substantially pentagonal shape and into which the fifth connection terminal 45 is inserted. These terminal insertion holes 111A to 115A communicate with the element insertion hole 17A at respective sides thereof facing the center of the ceramic separator 13A.

Furthermore, in the second embodiment, the first terminal insertion hole 111A has a first main insertion hole 116A having a substantially pentagonal shape and a first relief hole 111cA which is surrounded by an outline connecting the end of an upper side 111aA and the end of a right side 111bA of the first main insertion hole 116A. The first relief hole 111cA is located radially outward of the first main insertion hole 116A and has a shape (an arc shape of a ¾ circle) similar to that of the second relief hole 86A of the ceramic sleeve 67A.

The second terminal insertion hole 112A has a second main insertion hole 117A having a substantially rectangular shape; a second relief hole 112cA which is surrounded by an outline connecting the end of an upper side 112aA and the end of a left side 112bA of the second main insertion hole 117A and is located radially outward of the second main insertion hole 117A and which has a shape (an arc shape of a ¾ circle) similar to that of the first relief hole 85A of the ceramic sleeve 67A; and a third relief hole 112eA which is surrounded by an outline connecting the end of the upper side 112aA and the end of a right side 112dA and is located radially outward of the second main insertion hole 117A and which has a shape (an arc shape of a ¾ circle) similar to that of the second relief hole 86A of the ceramic sleeve 67A.

The third terminal insertion hole 113A has a third main insertion hole 118A having a substantially pentagonal shape and a fourth relief hole 113cA which is surrounded by an outline connecting the end of an upper side 113aA and the end of a left side 113bA of the third main insertion hole 118A. The fourth relief hole 113cA is located radially outward of the third main insertion hole 118A and has a shape (an arc shape of a ¾ circle) similar to that of the first relief hole 85A of the ceramic sleeve 67A.

The fourth terminal insertion hole 114A has a fourth main insertion hole 119A having a substantially pentagonal shape and a fifth relief hole 114cA which is surrounded by an outline connecting the end of a lower side 114aA and the end of a right side 114bA of the fourth main insertion hole 119A. The fifth relief hole 114cA is located radially outward of the fourth main insertion hole 119A and has a shape (an arc shape of a ¾ circle) similar to that of the fourth relief hole 88A of the ceramic sleeve 67A.

The fifth terminal insertion hole 115A has a fifth main insertion hole 120A having a substantially pentagonal shape and a sixth relief hole 115cA which is surrounded by an outline connecting the end of a lower side 115aA and the end of a left side 115bA of the fifth main insertion hole 120A. The sixth relief hole 115cA is located radially outward of the fifth main insertion hole 120A and has a shape (an arc shape of a ¾ circle) similar to that of the third relief hole 87A of the ceramic sleeve 67A.

Figure 17:
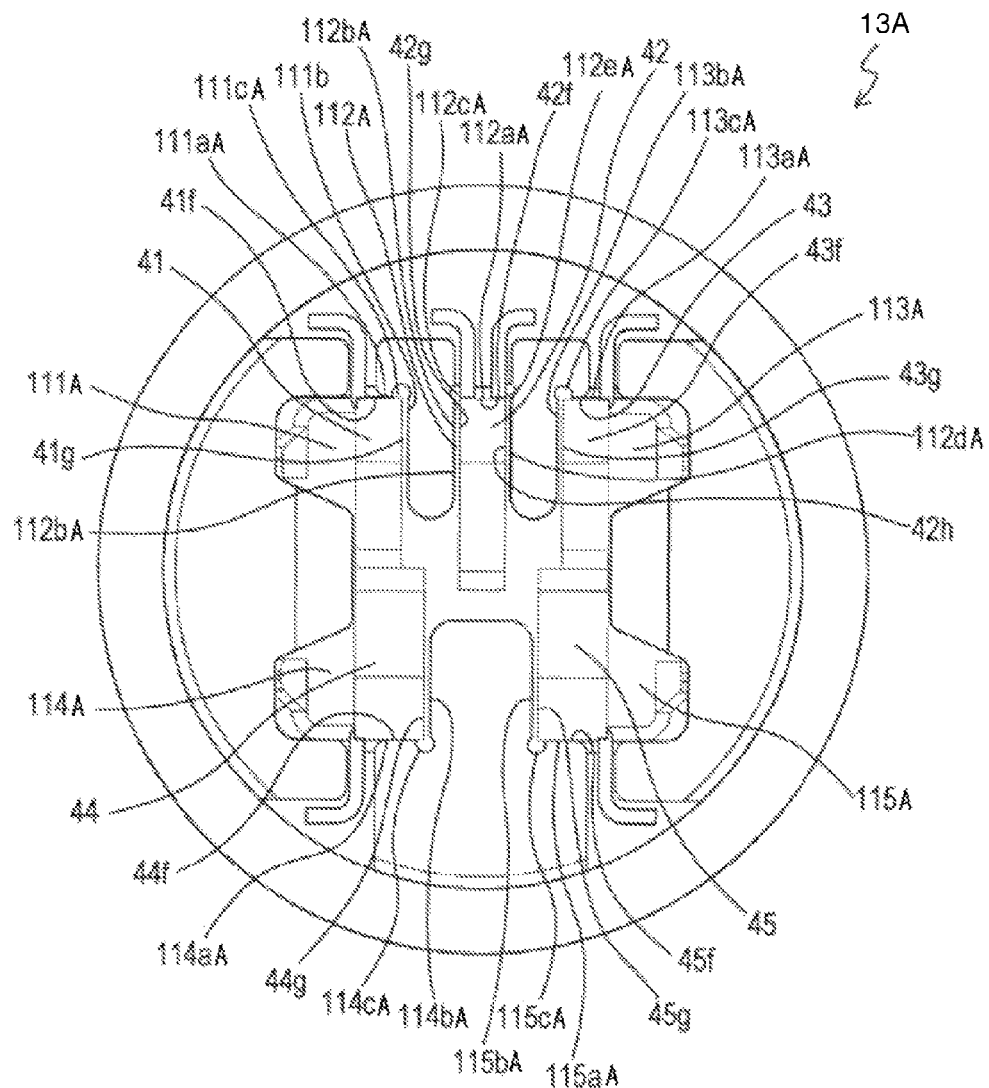
FIG. 17 is a plan view of the ceramic separator of the second embodiment viewed from the rear side, showing a state in which the connection terminals are disposed therein.

As shown in FIG. 17, the elongated first connection terminal 41 extending in the axial direction of the ceramic separator 13A (a direction perpendicular to the paper on which FIG. 17 appears) is disposed in the first terminal insertion hole 111A. The elongated second connection terminal 42 extending in the axial direction of the ceramic separator 13A is disposed in the second terminal insertion hole 112A. The elongated third connection terminal 43 extending in the axial direction of the ceramic separator 13A is disposed in the third terminal insertion hole 113A. The elongated fourth connection terminal 44 extending in the axial direction of the ceramic separator 13A is disposed in the fourth terminal insertion hole 114A. The elongated fifth connection terminal 45 extending in the axial direction of the ceramic separator 13A is disposed in the fifth terminal insertion hole 115A.

In the second embodiment, as shown in FIG. 17, as viewed from the axial direction of the ceramic separator 13A, the connection terminals 41 to 45 described above are configured such that their edges do not come into contact with inner peripheral surfaces of the terminal insertion holes 111A to 115A, respectively.

Specifically, as shown in FIG. 17, by virtue of the first relief hole 111cA, an edge formed by the upper end 41f and the right end 41g of the first connection terminal 41 does not contact an inner peripheral surface of the first terminal insertion hole 111A.

Also, by virtue of the second relief hole 112cA, an edge formed by the upper end 42f and the left end 42g of the second connection terminal 42 does not contact an inner peripheral surface of the second terminal insertion hole 112A. By virtue of the third relief hole 112eA, an edge formed by the upper end 42f and the right end 42h of the second connection terminal 42 does not contact an inner peripheral surface of the second terminal insertion hole 112A.

Also, by virtue of the fourth relief hole 113cA, an edge formed by the upper end 43f and the left end 43g of the third connection terminal 43 does not contact an inner peripheral surface of the third terminal insertion hole 113A.

Also, by virtue of the fifth relief hole 114cA, an edge formed by the lower end 44f and the right end 44g of the fourth connection terminal 44 does not contact an inner peripheral surface of the fourth terminal insertion hole 114A.

Furthermore, by virtue of the sixth relief hole 115cA, an edge formed by the lower end 45f and the left end 45g of the fifth connection terminal 45 does not contact an inner peripheral surface of the fifth terminal insertion hole 115A.

i) Next, the effects of the second embodiment will be described.

In the second embodiment, the element insertion hole 81A of the ceramic sleeve 67A has first to fourth relief holes 85A to 88A, each having an arc shape of a ¾ circle, at four corners, respectively, of the main insertion hole 83A having a quadrate cross section, and the element insertion hole 101A of the ceramic holder 61A has first to fourth relief holes 105A to 108A, each having an arc shape of a ¾ circle, at four corners, respectively, of the main insertion hole 103A having a quadrate cross section.

That is, the main insertion holes 83A and 103A do not have radiused edges. Therefore, the dimensions of the detection element 5 to be inserted into the main insertion holes 83A and 103A can be substantially equal to the dimensions of the main insertion holes 83A and 103A. As a result, a clearance between a side surface of the detection element 5 and corresponding inner peripheral surfaces of the element insertion holes 81A and 101A can be small, thereby reducing play of the detection element 5 within the element insertion holes 81A and 101A.

The two sides of each of the main insertion holes 83A and 103A which are connected to the outline of each of the first to fourth relief holes 85A to 88A and 105A to 108A do not reach an intersection of extension lines of the two sides. Further, the area of each of the first to fourth relief holes 85A to 88A and 105A to 108A is greater than the area of a triangle surrounded by the extension lines of the two sides and a straight line connecting the ends of the two sides of each of the main insertion holes 83A and 103A.

Thus, the first to fourth relief holes 85A to 88A and 105A to 108A protrude further radially outward of the main insertion holes 83A and 103A. As a result, the shortest distance between the outline of each of the first to fourth relief holes 85A to 88A and 105A to 108A and the intersection of the extension lines increases. Therefore, when the detection element 5 is inserted into the main insertion holes 83A and 103A, contact of edges of the detection element with the outlines of the first to fourth relief holes 85A to 88A and 105A to 108A can be reliably prevented.

Also, since those ends of the two sides of each of the main insertion holes 83A and 103A which are connected to the outline of each of the first to fourth relief holes 85A to 88A and 105A to 108A further approach each other, the two sides can be increased in length. Therefore, the two inner peripheral surfaces of each of the main insertion holes 83A and 103A, which include the two sides, face two corresponding side surfaces of the detection element 5 over respectively increased ranges, thereby further reducing play of the detection element 5 within the element insertion holes 81A and 101A.

In the second embodiment, the first to fifth terminal insertion holes 111A to 115A of the ceramic separator 13A have the first to sixth relief holes 111cA, 112cA, 112eA, 113cA, 114cA and 115cA, each having an arc shape of a ¾ circle, at edges (corners) of the first to fifth main insertion holes 116A to 120A.

That is, the first to fifth main insertion holes 116A to 120A do not have radiused edges. Therefore, the dimensions of the first to fifth connection terminals 41 to 45 to be inserted into the first to fifth main insertion holes 116A to 120A, respectively, can be substantially equal to the dimensions of the first to fifth main insertion holes 116A to 120A. As a result, a clearance between side surfaces of the first to fifth connection terminals 41 to 45 and corresponding inner peripheral surfaces of the first to fifth terminal insertion holes 111A to 115A can be small, thereby reducing play of the first to fifth connection terminals 41 to 45 within the first to fifth terminal insertion holes 111A to 115A, respectively.

The two sides of each of the first to fifth main insertion holes 116A to 120A which are connected to the outline of each of the first to sixth relief holes 111cA to 115cA do not reach an intersection of extension lines of the two sides. Further, the area of each of the first to sixth relief holes 111cA to 115cA is greater than the area of a triangle surrounded by the extension lines of the two sides and a straight line that connects the ends of the two sides of each of the first to fifth main insertion holes 116A to 120A.

Thus, the first to sixth relief holes 111cA to 115cA protrude further radially outward of the first to fifth main insertion holes 116A to 120A. As a result, the shortest distance between the outline of each of the first to sixth relief holes 111cA to 115cA and the intersection of the extension lines increases. Therefore, when the first to fifth connection terminals 41 to 45 are inserted into the first to fifth main insertion holes 116A to 120A, respectively, contact of edges of the first to fifth connection terminals 41 to 45 with the outlines of the first to sixth relief holes 111cA to 115cA can be reliably prevented.

Also, since the ends of the two sides of each of the first to fifth main insertion holes 116A to 120A which are connected to the outline of each of the first to sixth relief holes 111cA to 115cA further approach each other, the two sides can be increased in length. Therefore, the two inner peripheral surfaces of each of the main insertion holes 116A to 120A, which include the two sides, face two corresponding side surfaces of each of the first to fifth connection terminals 41 to 45 over respectively increased ranges, thereby further reducing play of the first to fifth connection terminals 41 to 45 within the first to fifth terminal insertion holes 111A to 115A, respectively.

Furthermore, the second embodiment has the following advantage: since the outlines of the relief holes 85A to 88A, 105A to 108A, 111cA, 112cA, 112eA, 113cA, 114cA and 115cA are smoothly formed (in an arc shape), cracks are further unlikely to generate in the ceramic members.

Modifications

Next, modifications of the first and second embodiments will be described.

Figure 18A:
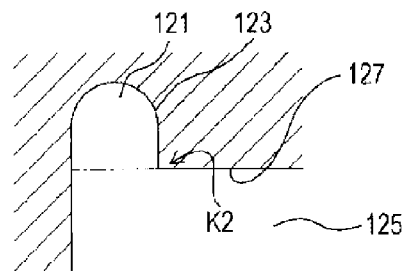
FIGS. 18A to 18H are explanatory views showing the cross-sectional shapes (shapes of cross sections taken perpendicularly to the direction of the axial line) of relief holes in modifications 1 to 8.
Figure 18B:
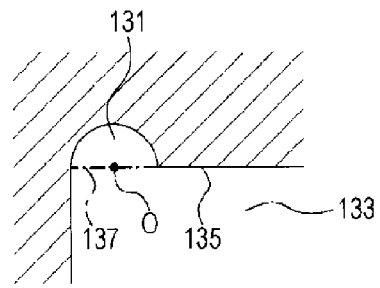
Figure 18C:
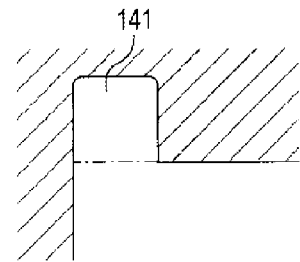

First, modifications 1 to 8 will be described. Since modifications 1 to 8 differ from the first embodiment in the cross-sectional shape (shape of cross section taken perpendicularly to the axial direction) of the relief hole, only the differences are described.

a) As shown in FIG. 18A, in modification 1, the element insertion holes and the terminal insertion holes of the ceramic sleeve, the ceramic holder, and the ceramic separator described above have relief holes 121, each having a cross-sectional shape substantially similar to that of the embodiments described above. However, an edge K2 where an outline 123 of the relief holes 121 and a first long side 127 of a main insertion hole 125 intersect is not radiused.

b) As shown in FIG. 18B, in modification 2, the element insertion holes and the terminal insertion holes of the ceramic sleeve, the ceramic holder, and the ceramic separator described above have relief holes 131, each having a semicircular cross section. A center O of the semicircle is the center of an extension line 137 of a first long side 135 of a main insertion hole 133.

c) As shown in FIG. 18C, in modification 3, the element insertion holes and the terminal insertion holes of the ceramic sleeve, the ceramic holder, and the ceramic separator described above have relief holes 141, each having a substantially quadrate (e.g., square) cross section.

Figure 18D:
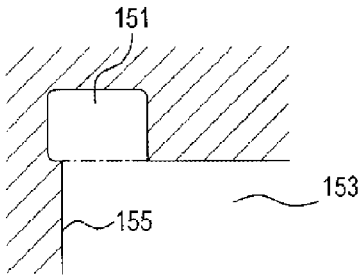

The edges of the relief hole 141 are radiused; i.e., smoothly curved (in an outwardly convex form).

d) As shown in FIG. 18D, in modification 4, the element insertion holes and the terminal insertion holes of the ceramic sleeve, the ceramic holder, and the ceramic separator described above have relief holes 151, each having a substantially quadrate (rectangular) cross section. Particularly, the relief hole 151 protrudes radially outward (leftward in FIG. 18D) of a first short side 155 of a main insertion hole 153.

Figure 18E:
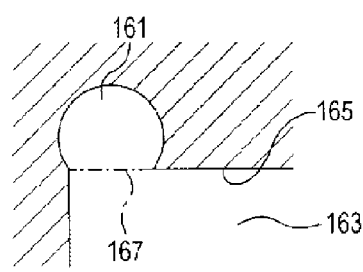
Figure 18F:
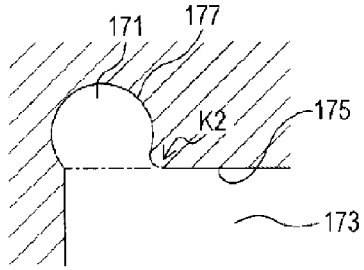
Figure 18G:
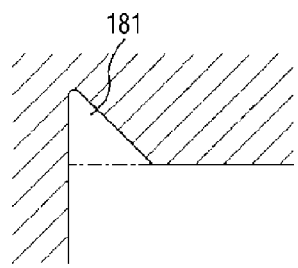

The edges of the relief hole 151 are radiused; i.e., smoothly curved (in an outwardly convex form).

e) As shown in FIG. 18E, in modification 5, the element insertion holes and the terminal insertion holes of the ceramic sleeve, the ceramic holder, and the ceramic separator described above have relief holes 161, each having a substantially circular cross section. Particularly, the relief hole 161 has an arc shape; i.e., a partially missing circular shape (specifically, a circle is truncated at a bottom portion by an extension line 167 of a first long side 165 of a main insertion hole 163).

f) As shown in FIG. 18F, in modification 6, a relief hole 171 has an arc shape substantially similar to that of the relief hole 161 of modification 5; however, an edge K2 at the intersection of an outline 177 of the relief hole 171 and a first ling side 175 of a main insertion hole 173 is radiused.

g) As shown in FIG. 18G, in modification 7, the element insertion holes and the terminal insertion holes of the ceramic sleeve, the ceramic holder, and the ceramic separator described above have relief holes 181, each having a substantially triangular cross section.

Figure 18H:
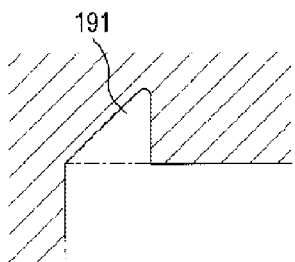

The edge at an apex of the relief hole 181 is radiused; i.e., smoothly curved (in an outwardly convex form).

h) As shown in FIG. 18H, in modification 8, a relief hole 191 has a triangular cross section substantially similar to that of the relief hole 181 of modification 7, but is oriented horizontally in reverse.

Figure 19A:
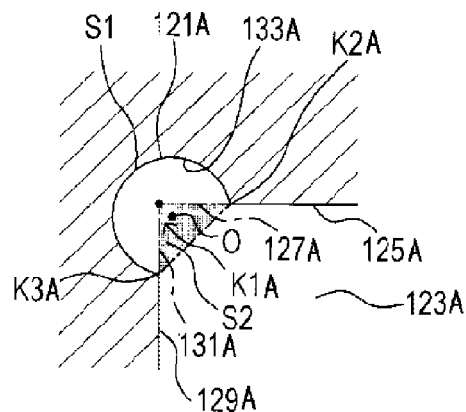
FIGS. 19A to 19F are explanatory views showing the cross-sectional shapes (shapes of cross sections taken perpendicularly to the direction of the axial line) of relief holes in modifications 1A to 6A.

Next, modifications 1A to 6A will be described. Since modifications 1A to 6A differ from the second embodiment in the cross-sectional shape (shape of cross section taken perpendicularly to the axial direction) of the relief hole, only the differences are described.

i) As shown in FIG. 19A, in modification 1A, the element insertion holes and the terminal insertion holes of the ceramic sleeve, the ceramic holder, and the ceramic separator described above have relief holes 121A, each having a cross-sectional shape (arc shape) substantially similar to that of the embodiment described above. However, in modification 1A, the center O of the circle is located within a main insertion hole 123A.

Figure 19B:
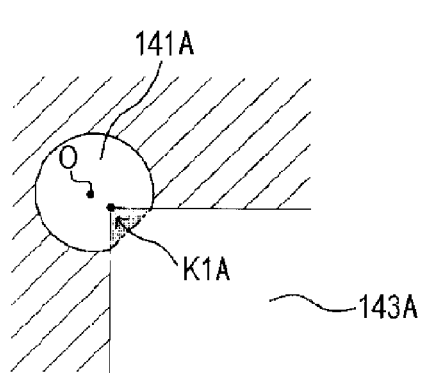
Figure 19C:
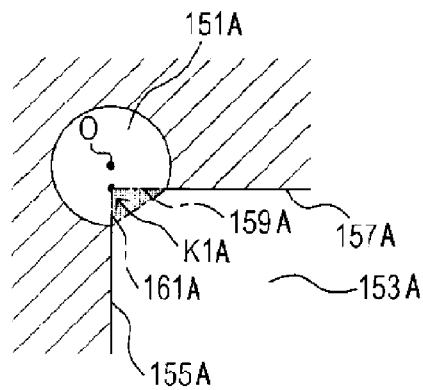

In this case also, the area S1 of the relief hole 121A is greater than the area S2 of a triangle defined by the intersection K1A of an extension line 127A of a first long side 125A and an extension line 131A of a first short side 129A, the intersection K2A of the first long side 125A and an outline 133A of the relief hole 121A, and the intersection K3A of the first short side 129A and the outline 133A of the relief hole 121A (the same also applies in the following modifications).

j) As shown in FIG. 19B, in modification 2A, the element insertion holes and the terminal insertion holes of the ceramic sleeve, the ceramic holder, and the ceramic separator described above have relief holes 141A, each having an arc cross-sectional shape substantially similar to that of the embodiment described above. The center O of the relief hole 141A is located externally of a main insertion hole 143A.

k) As shown in FIG. 19C, in modification 3A, the element insertion holes and the terminal insertion holes of the ceramic sleeve, the ceramic holder, and the ceramic separator described above have relief holes 151A, each having an arc cross-sectional shape substantially similar to that of the embodiment described above.

Figure 19D:
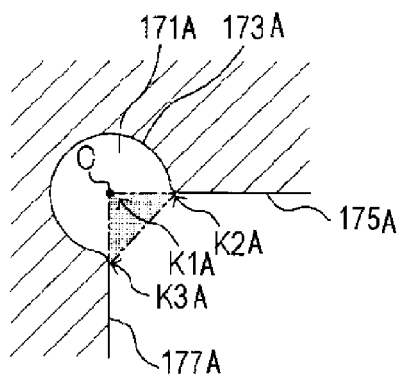

The center O of the relief hole 151A is located externally of a main insertion hole 153A on a further extension of an extension line 161A of a first short side 155A (and may be offset horizontally from the extension line). Therefore, an extension line 159A of a first long side 157A is longer than the extension line 161A of the first short side 155A.

l) As shown in FIG. 19D, in modification 4A, the element insertion holes and the terminal insertion holes of the ceramic sleeve, the ceramic holder, and the ceramic separator described above have relief holes 171A, each having an arc cross-sectional shape substantially similar to that of the embodiment described above.

Particularly, in the relief hole 171A, the edge at the intersection K2A of its outline 173A and a first long side 175A is radiused; i.e., smoothly curved (in an outwardly convex form). Similarly, the edge at the intersection K3A of a first short side 177A and the outline 173A of the relief hole 171A is radiused; i.e., smoothly curved (in an outwardly convex form).

Figure 19E:
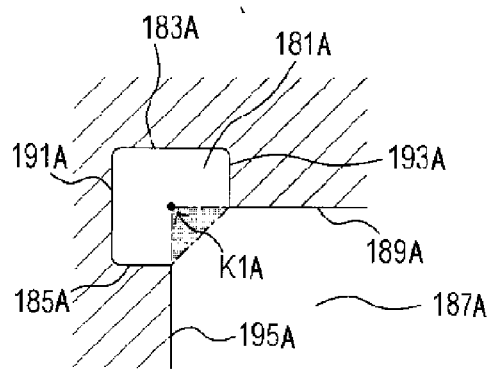

Smoothly curving the edges is applicable to the embodiments described above and other modifications.

m) As shown in FIG. 19E, in modification 5A, the element insertion holes and the terminal insertion holes of the ceramic sleeve, the ceramic holder, and the ceramic separator described above have relief holes 181A, each having a partially missing, substantially quadrate (square) cross section.

Specifically, the relief hole 181A is shaped such that upper and lower sides 183A and 185A of a rectangle are parallel to a first long side 189A of a main insertion hole 187A and such that left and right sides 191A and 193A of the rectangle are parallel to a first short side 195A of the main insertion hole 187A.

Figure 19F:
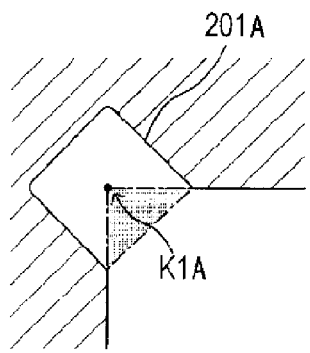
Figure 20:
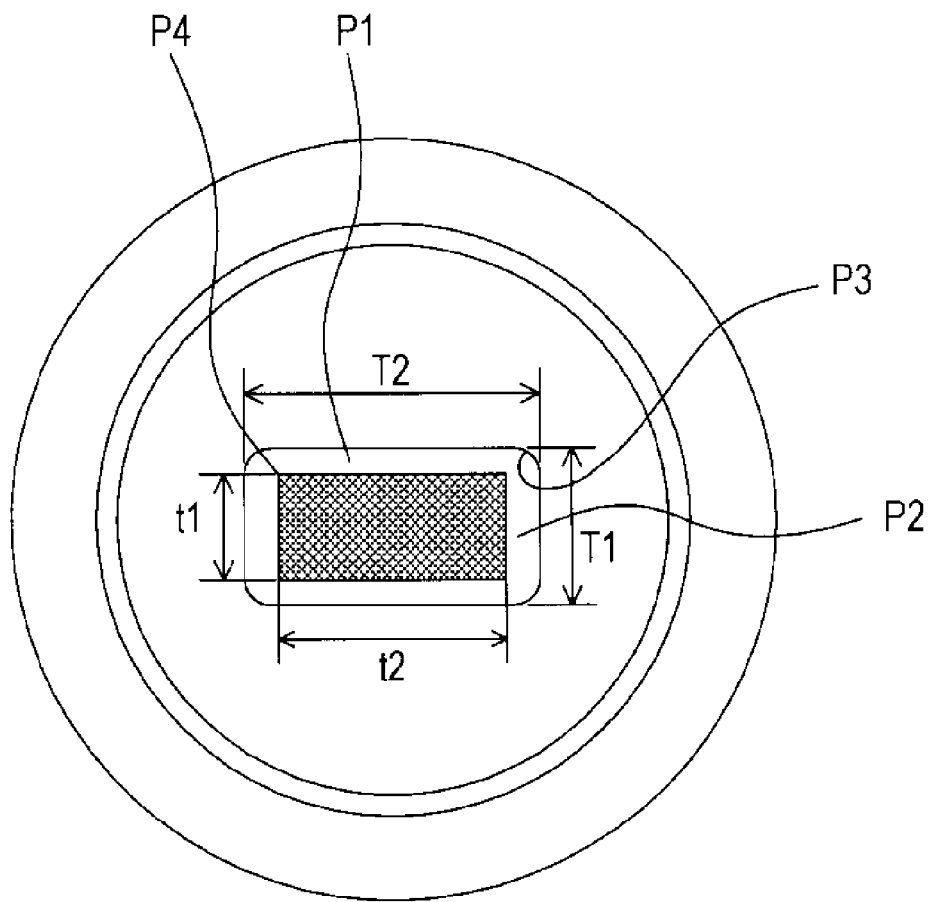
FIG. 20 is an explanatory view showing a conventional technique.

Edges of the relief hole 181A are radiused; i.e., smoothly curved (in an outwardly convex form).

n) As shown in FIG. 19F, in modification 6A, the element insertion holes and the terminal insertion holes of the ceramic sleeve, the ceramic holder, and the ceramic separator described above have relief holes 201A, each having a partially missing, substantially quadrate (square) cross section.

The relief hole 201A of modification 6A is shaped such that the relief hole 181A of the modification 5A is inclined.

The present invention is not limited to the above embodiments and modifications thereof, and may be embodied in various other forms without departing from the spirit and scope of the claims appended hereto.

(1) For example, in the above embodiments, the ceramic sleeve, the ceramic holder, and the ceramic separator have a plurality of relief holes. However, a single relief hole may be provided; i.e., no particular limitation is imposed on the number of relief holes.

(2) Also, in the above embodiments, all of the ceramic members; i.e., all of the ceramic sleeve, the ceramic holder, and the ceramic separator, have relief holes; however, instead, at least a single ceramic member may have relief holes.

(3) Also, the above embodiments are described with application to a full range air/fuel ratio sensor. However, the present invention is not limited thereto. The invention may be applied to various gas sensors, such as λ sensors, oxygen sensors, and $NO_x$ sensors, and temperature sensors for detecting temperature. Such applications yield effects similar to those obtained by the above embodiments.

This application is based on Japanese Patent Application No. 2013-023680 filed Feb. 8, 2013, Japanese Patent Application No. 2013-023683 filed Feb. 8, 2013 and Japanese Patent Application No. 2013-225507 filed Oct. 30, 2013, incorporated herein by reference in their entirety.

What is claimed is:

1. A gas sensor comprising:
a metallic shell having a through hole,
a platelike detection element extending in an axial direction; and
a ceramic member positioned within the through hole and having an element insertion hole into which the detection element is inserted, wherein when the ceramic member is viewed from the axial direction, the element insertion hole has a main insertion hole having a substantially quadrate shape surrounded by four sides, and a relief hole surrounded by an outline connecting ends of two adjacent sides of the four sides of the main insertion hole, and located radially outward of the main insertion hole so as to communicate with the main insertion hole, and said gas sensor further comprising a tubular casing attached to a rear end portion of the metallic shell, a forward end of the platelike detection element protruding from a forward end of the metallic shell.

2. The gas sensor as claimed in claim 1, wherein of the two sides of the main insertion hole connected to the outline of the relief hole, one side reaches an intersection with an extension line of the other side.

3. The gas sensor as claimed in claim 2, wherein the outline of the relief hole is smoothly formed from the end of the one side to the end of the other side.

4. The gas sensor as claimed in claim 1, wherein the two sides of the main insertion hole connected to the outline of the relief hole do not reach an intersection of extension lines of the two sides, and an area of the relief hole is greater than an area of a triangle surrounded by the extension lines of the two sides of the main insertion hole and a straight line connecting the ends of the two sides of the main insertion hole.

5. The gas sensor as claimed in claim 4, wherein the outline of the relief hole is smoothly formed.

6. A gas sensor comprising:

a platelike detection element extending in an axial direction; and a ceramic member surrounding a rear end portion of the detection element and having a substantially quadrate element insertion hole into which the detection element is inserted, and a terminal insertion hole which is located radially outward of the element insertion hole and communicates with the element insertion hole and into which a connection terminal electrically connected to the detection element is inserted, wherein when the ceramic member is viewed from the axial direction, the terminal insertion hole has a main insertion hole having a substantially polygonal shape surrounded by a plurality of sides, and a relief hole surrounded by an outline connecting ends of two adjacent sides of the plurality of sides of the main insertion hole, and located radially outward of the main insertion hole so as to communicate with the main insertion hole.

7. The gas sensor as claimed in claim 6, wherein of the two sides of the main insertion hole connected to the outline of the relief hole, one side reaches an intersection with an extension line of the other side.

8. The gas sensor as claimed in claim 7, wherein the outline of the relief hole is smoothly formed from the end of the one side to the end of the other side.

9. The gas sensor as claimed in claim 6, wherein the two sides of the main insertion hole connected to the outline of the relief hole do not reach an intersection of extension lines of the two sides, and an area of the relief hole is greater than an area of a triangle surrounded by the extension lines of the two sides of the main insertion hole and a straight line connecting the ends of the two sides of the main insertion hole.

10. The gas sensor as claimed in claim 9, wherein the outline of the relief hole is smoothly formed.

* * * * *